(12) United States Patent
Bakale et al.

(10) Patent No.: US 12,364,686 B2
(45) Date of Patent: Jul. 22, 2025

(54) SPHINGOSINE 1 PHOSPHATE RECEPTOR MODULATORS

(71) Applicant: RECEPTOS LLC, New York, NY (US)

(72) Inventors: Roger Bakale, Summit, NJ (US); Jeff Schkeryantz, Summit, NJ (US); Maurice Marsini, Summit, NJ (US)

(73) Assignee: Receptos LLC, New York, NY (US)

( * ) Notice: Subject to any disclaimer, the term of this patent is extended or adjusted under 35 U.S.C. 154(b) by 527 days.

(21) Appl. No.: 17/914,707

(22) PCT Filed: Mar. 25, 2021

(86) PCT No.: PCT/US2021/024179
§ 371 (c)(1),
(2) Date: Sep. 26, 2022

(87) PCT Pub. No.: WO2021/195396
PCT Pub. Date: Sep. 30, 2021

(65) Prior Publication Data
US 2023/0149367 A1     May 18, 2023

Related U.S. Application Data

(60) Provisional application No. 63/018,327, filed on Apr. 30, 2020, provisional application No. 63/001,073, filed on Mar. 27, 2020.

(51) Int. Cl.
*A61K 31/4245*     (2006.01)
(52) U.S. Cl.
CPC ............................... *A61K 31/4245* (2013.01)
(58) Field of Classification Search
CPC ..................... C07D 271/06; A61K 31/4245
See application file for complete search history.

(56) References Cited

U.S. PATENT DOCUMENTS

2020/0085795 A1*   3/2020   Meadows ............... A61P 25/16

FOREIGN PATENT DOCUMENTS

| JP | 2009524611 A | 7/2009 |
|----|--------------|--------|
| JP | 2013510885 A | 3/2013 |
| JP | 2017532294 A | 11/2017 |
| WO | 2009/151529 A1 | 12/2009 |
| WO | 2018/208855 A1 | 11/2018 |
| WO | 2018231745 A1 | 12/2018 |

OTHER PUBLICATIONS

International Search Report and Written Opinion mailed Jun. 2, 2021, in International Application No. PCT/US2021/024179, filed Mar. 25, 2021, 8 pages.

* cited by examiner

*Primary Examiner* — Kamal A Saeed
(74) *Attorney, Agent, or Firm* — Seed IP Law Group LLP

(57) ABSTRACT

Compounds are provided having the structure of Formula (I): (Formula (I)) or a pharmaceutically acceptable salt, homolog, hydrate or solvate thereof, wherein R is as defined herein. Such compounds serve as modulators of the sphingosine-1-phosphate receptor, and have utility for treatment of a malcondition for which activation of this receptor is medically indicated.

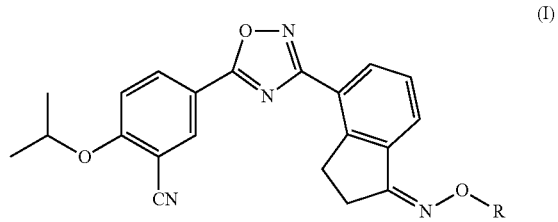

10 Claims, No Drawings

SPHINGOSINE 1 PHOSPHATE RECEPTOR MODULATORS

BACKGROUND

Technical Field

Modulators of the sphingosine-1-phosphate receptor are provided for treatment of a malcondition for which activation of the same is medically indicated.

Description of the Related Art

The $S1P_1/EDG_1$ receptor is a G-protein coupled receptor (GPCR) and is a member of the endothelial cell differentiation gene (EDG) receptor family. Endogenous ligands for EDG receptors include lysophospholipids, such as sphingosine-1-phosphate (SIP). Like all GPCRs, ligation of the receptor propagates second messenger signals via activation of G-proteins (alpha, beta and gamma). Development of small molecule $S1P_1$ agonists and antagonists has provided insight into some physiological roles of the $S1P_1/S1P$-receptor signaling system. To this end, S1P receptors are divided into five subtypes (i.e., $S1P_1$, $S1P_2$, $S1P_3$, $S1P_4$ and $S1P_5$), which subtypes are expressed in a wide variety of tissues and exhibit different cell specificity. Agonism of the $S1P_1$ receptor perturbs lymphocyte trafficking, sequestering them in lymph nodes and other secondary lymphoid tissue. This leads to rapid and reversible lymphopenia, and is probably due to receptor ligation on both lymphatic endothelial cells and lymphocytes themselves (Rosen et al, *Immunol. Rev.*, 195:160-177, 2003).

BRIEF SUMMARY

In brief, modulators of the sphingosine-1-phosphate receptor are provided for treatment of a malcondition for which activation of the same is medically indicated.

In one embodiment, a compound is provided having the structure of Formula (I):

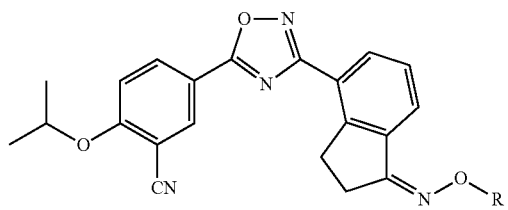

(I)

or a pharmaceutically acceptable salt, homolog, hydrate or solvate thereof, wherein R is as defined below.

DETAILED DESCRIPTION OF THE DISCLOSURE

As used in the specification and the appended claims, the singular forms "a," "an" and "the" include plural referents unless the context clearly dictates otherwise. Further, the words "comprising," "including" and "having" are open-ended terms as used herein, and do not preclude the existence of additional elements or components.

The present invention is directed to compounds which modulate an S1P receptor, as well as to related products and methods for their preparation and use. S1P receptors are divided into five subtypes (i.e., $S1P_1$, $S1P_2$, $S1P_3$, $S1P_4$ and $S1P_5$), which subtypes are expressed in a wide variety of tissues and exhibit different cell specificity. The compounds disclosed herein modulate one or more of these subtypes. In one embodiment, the compounds are "$S1P_1$" modulators as they modulate subtype 1 of a sphingosine-1-phosphate receptor. In another embodiment, the compounds modulate subtype 1 and another subtype, such as subtype 5. As used herein, an "$S1P_1$ modulator" is understood to encompass compounds that modulate the $S1P_1$ subtype alone, or modulate the $S1P_1$ subtype as well as one or more other subtypes. In one embodiment, an $S1P_1$ modulator modulates both the $S1P_1$ subtype and the $S1P_5$ subtype.

As used herein, a "modulator" of the $S1P_1$ receptor is a compound which, when administered to a subject, provides the desired integration with the target receptor, either by way of the compound acting directly on the receptor itself, or by way of a metabolite of the compound acting on the receptor. Upon administration to a subject, the compounds of this invention modulate the $S1P_1$ receptor by activating on the receptor for signal transduction. Such compounds are also referred to herein as "agonists" or "$S1P_1$ agonists". Such $S1P_1$ agonists can be selective for action on $S1P_1$. For example, a compound selective for action on $S1P_1$ acts at a lower concentration on $S1P_1$ than on other subtypes of the S1P receptor family.

Receptor agonists may be classified as either orthosteric or allosteric, and $S1P_1$ agonists of this invention include both classifications, either by way of the compound or by way of a metabolite of the compound acting on the receptor. In certain embodiments, compounds of the invention are orthostatic agonists. An orthosteric agonist binds to a site in the receptor that significantly overlaps with the binding of the natural ligand and replicates the key interactions of the natural ligand with the receptor. An orthosteric agonist will activate the receptor by a molecular mechanism similar to that of the natural ligand, will be competitive for the natural ligand, and will be competitively antagonized by pharmacological agents that are competitive antagonists for the natural ligand.

In certain other embodiments, compounds of the invention are allosteric agonists. An allosteric agonist binds to a site in the receptor that makes some significant interactions that are partly or wholly non-overlapping with the natural ligand. Allosteric agonists are true agonists and not allosteric potentiators. Consequently, they activate receptor signaling alone and without a requirement for a sub-maximal concentration of the natural ligand. Allosteric agonists may be identified when an antagonist known to be competitive for the orthosteric ligand shows non-competitive antagonism. The allosteric agonist site can also be mapped by receptor mutagenesis.

In one embodiment, a compound is provided having the structure of Formula (I):

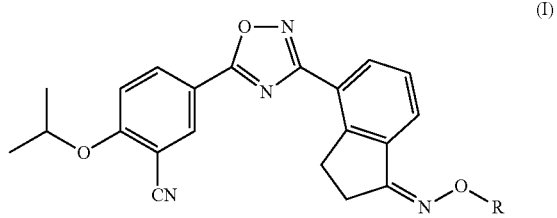

(I)

or a pharmaceutically acceptable salt, homolog, hydrate or solvate thereof, wherein:

R is:
  alkyl;
  alkanediyl-NR$^1$R$^2$;
  alkanediyl-C(=O)OR$^1$; or
  heterocyclylalkyl; and R$^1$ and R$^2$ are independently H or C$_{1-4}$alkyl.

As used in Formula (I), the following terms have the meanings set forth below.

"Alkanediyl" means a divalent radical such as methylene (—CH$_2$—) derived from an alkyl group by removal of two hydrogen atoms. Accordingly, any alkyl group as defined herein constitutes an alkanediyl by removal of two hydrogen atoms to render a divalent radical.

"Alkyl" means straight chain, branched or cyclic alkyl group (cycloalkyl), saturated or unsaturated, having from 1 to about 20 carbon atoms (C$_{1-20}$ alkyl), and from 3 to 20 carbon atoms in the case of cycloalkyl. Alkyls are typically from 1 to 12 carbons (C$_{1-12}$ alkyl) or, in some embodiments, from 1 to 8 carbon atoms (C$_{1-8}$ alkyl) or, in some embodiments, from 1 to 4 carbon atoms (C$_{1-4}$ alkyl) or, in some embodiments, from 1 to 3 carbon atoms (C$_{1-3}$ alkyl). Examples of straight chain alkyl groups include, but are not limited to methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups.

Examples of unsaturated alkyls include alkenyl and alkynyl groups. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Alkenyl" means a straight chain, branched or cyclic alkyl group as defined above, wherein at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to CH=CH(CH$_3$), CH=C(CH$_3$)$_2$, C(CH$_3$)=CH$_2$, C(CH$_3$)=CH(CH$_3$), C(CH$_2$CH$_3$)=CH$_2$, vinyl, cyclohexenyl, cyclopentenyl, cyclohexadienyl, butadienyl, pentadienyl, and hexadienyl among others.

"Alkynyl" means a straight chain, branched or cyclic alkyl group as defined above, wherein at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), CH$_2$C≡CH, CH$_2$C≡C(CH$_3$), and CH$_2$C≡C(CH$_2$CH$_3$), among others.

"Heterocyclyl" means aromatic (heteroaryl) and non-aromatic ring compounds containing 3 or more ring members, of which one or more is a heteroatom. In some embodiments, heterocyclyl includes 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a C2-heterocyclyl can be a 5-membered ring with two carbon atoms and three heteroatoms, a 6-membered ring with two carbon atoms and four heteroatoms and so forth. Likewise a C4-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms. Heterocyclic rings include fused ring species, including those having fused aromatic and non-aromatic groups. They also includes polycyclic ring systems containing a heteroatom such as, but not limited to, quinuclidyl.

Representative heterocyclyls include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heterocyclylalkyl" means an alkyl group as defined above in which a hydrogen or carbon bond of the alkyl group is replaced with a bond to a heterocyclyl group as defined above.

"Heteroaryl" means an aromatic heterocyclyl containing 5 or more ring members, of which, one or more is a heteroatom. A heteroaryl group designated as a C2-heteroaryl can be a 5-membered ring with two carbon atoms and three heteroatoms, a 6-membered ring with two carbon atoms and four heteroatoms and so forth. Likewise a C4-heteroaryl can be a 5-membered ring with one heteroatom, a 6-membered ring with two heteroatoms, and so forth. The number of carbon atoms plus the number of heteroatoms sums up to equal the total number of ring atoms.

Representative heteroaryls include, but are not limited to, pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. Heteroaryls also include fused ring compounds, such as when at least one ring, but not necessarily all rings, are aromatic, including tetrahydroquinolinyl, tetrahydroisoquinolinyl, indolyl and 2,3-dihydro indolyl.

"Heteroarylalkyl" means an alkyl group as defined above in which a hydrogen or carbon bond of the alkyl group is replaced with a bond to a heteroaryl group as defined above.

In one embodiment, a compound is provided having the structure of Formula (I), or a pharmaceutically acceptable salt, homolog, hydrate or solvate thereof, wherein R is alkyl, and in a more specific embodiment alkyl is methyl, ethyl, propryl, isopropyl, n-butyl, sec-butyl, iso-butyl, or tert-butyl.

In one embodiment, a compound is provided having the structure of Formula (I), or a pharmaceutically acceptable salt, homolog, hydrate or solvate thereof, wherein R is alkanediyl-NR$^1$R$^2$, where R$^1$ and R$^2$ are independently H or C$_{1-4}$alkyl.

In one embodiment, a compound is provided having the structure of Formula (I), or a pharmaceutically acceptable salt, homolog, hydrate or solvate thereof, wherein R is alkanediyl-C(=O)OR$^1$, where R$^1$ is H or C$_{1-4}$alkyl.

In one embodiment, a compound is provided having the structure of Formula (I), or a pharmaceutically acceptable salt, homolog, hydrate or solvate thereof, wherein R is heterocyclylalkyl, where heterocyclylalkyl is —(CH$_2$)$_{1-3}$-heterocyle and heterocyle is as defined herein.

Representative compounds of Formula (I) are listed in Table 1.

TABLE 1

| Cpd No. | Structure |
|---|---|
| 2 | 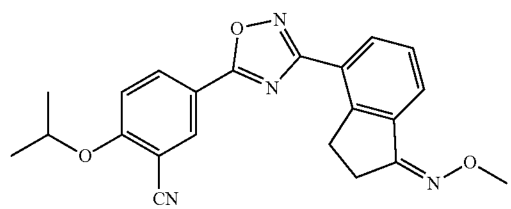 [SMILES: CO/N=C1/CCc2c1cccc2-c1noc(-c2ccc(OC(C)C)c(C#N)c2)n1] |
| 3 | 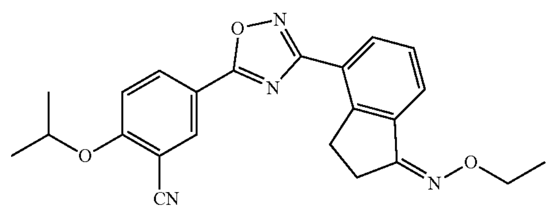 [SMILES: CCO/N=C1/CCc2c1cccc2-c1noc(-c2ccc(OC(C)C)c(C#N)c2)n1] |
| 4 | 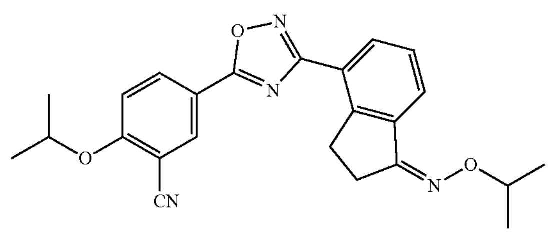 [SMILES: CC(C)O/N=C1/CCc2c1cccc2-c1noc(-c2ccc(OC(C)C)c(C#N)c2)n1] |
| 5 | 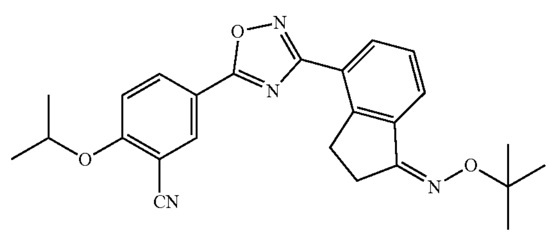 [SMILES: CC(C)Oc1ccc(-c2nc(-c3cccc4c3CC/C4=N/OC(C)(C)C)no2)cc1C#N] |
| 6 | 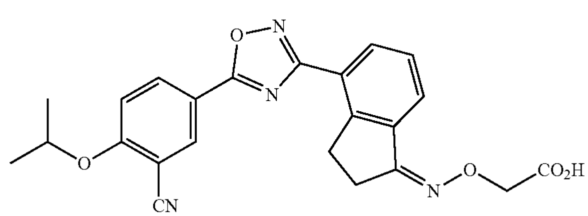 [SMILES: CC(C)Oc1ccc(-c2nc(-c3cccc4c3CC/C4=N/OCC(=O)O)no2)cc1C#N] |
| 7 | 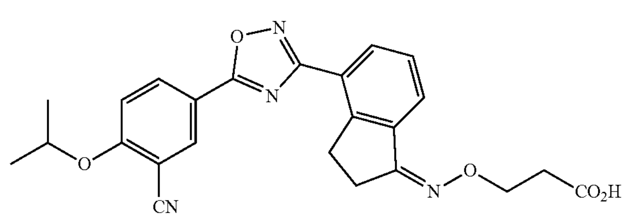 [SMILES: CC(C)Oc1ccc(-c2nc(-c3cccc4c3CC/C4=N/OCCC(=O)O)no2)cc1C#N] |

TABLE 1-continued

| Cpd No. | Structure |
|---------|-----------|
| 8 | 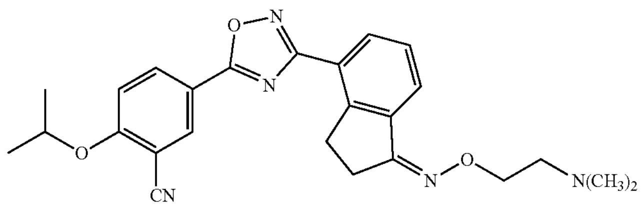 [SMILES: CC(C)Oc1ccc(-c2nc(-c3cccc4c3CC/C4=N/OCCN(C)C)no2)cc1C#N] |
| 9 | 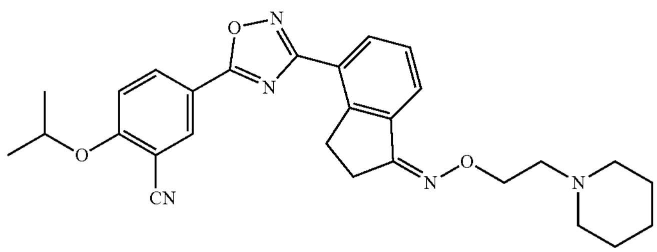 [SMILES: CC(C)Oc1ccc(-c2nc(-c3cccc4c3CC/C4=N/OCCN3CCCCC3)no2)cc1C#N] |
| 10 | 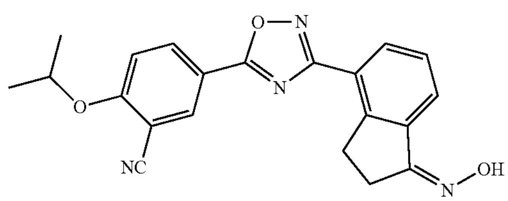 [SMILES: CC(C)Oc1ccc(-c2nc(-c3cccc4c3CC/C4=N/O)no2)cc1C#N] |
| 11 | 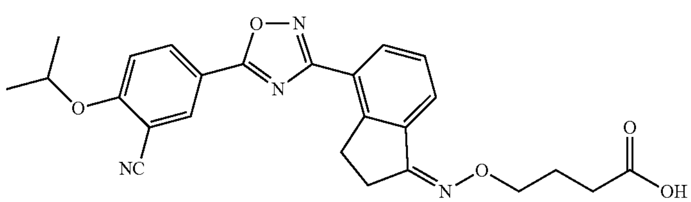 [SMILES: CC(C)Oc1ccc(-c2nc(-c3cccc4c3CC/C4=N/OCCCC(=O)O)no2)cc1C#N] |
| 12 | 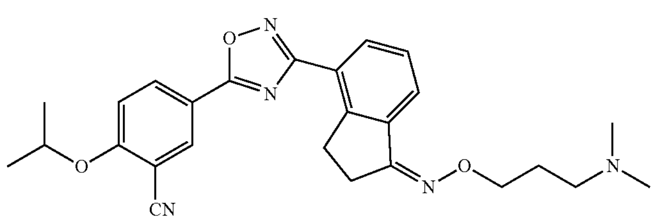 [SMILES: CC(C)Oc1ccc(-c2nc(-c3cccc4c3CC/C4=N/OCCCN(C)C)no2)cc1C#N] |
| 13 | 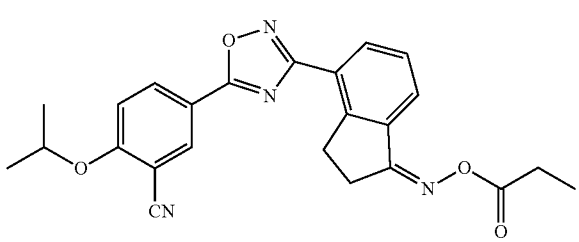 [SMILES: CCC(=O)O/N=C1/CCc2c1cccc2-c1noc(-c2ccc(OC(C)C)c(C#N)c2)n1] |
| 14 | 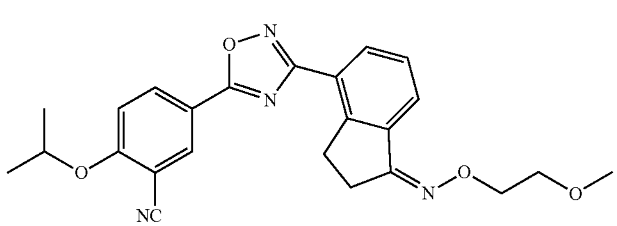 [SMILES: COCCO/N=C1/CCc2c1cccc2-c1noc(-c2ccc(OC(C)C)c(C#N)c2)n1] |

TABLE 1-continued
| Cpd No. | Structure |
|---|---|
| 15 | 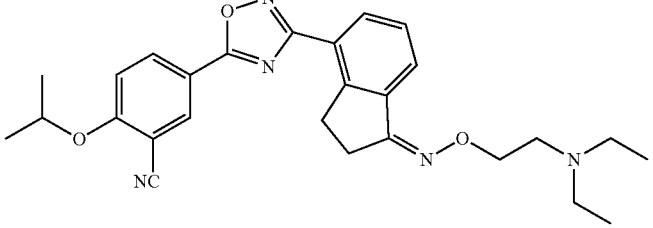 |
| 16 | 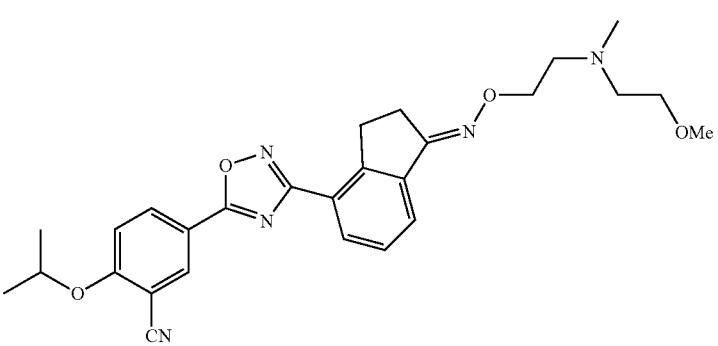 [SMILES: COCCN(C)CCO/N=C1\CCc2c1cccc2-c1noc(-c2ccc(OC(C)C)c(C#N)c2)n1] |
| 17 | 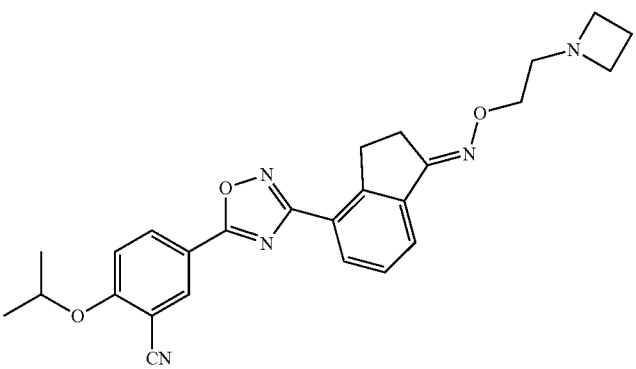 [SMILES: CC(C)Oc1ccc(-c2nc(-c3cccc4c3CC/C4=N\OCCN3CCC3)no2)cc1C#N] |
| 18 | 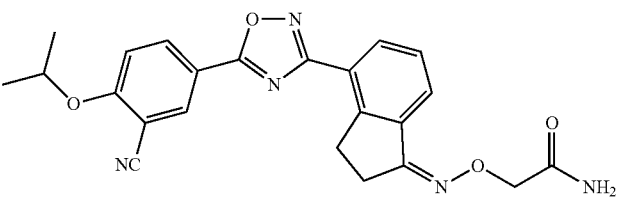 [SMILES: CC(C)Oc1ccc(-c2nc(-c3cccc4c3CC/C4=N/OCC(N)=O)no2)cc1C#N] |
| 19 | 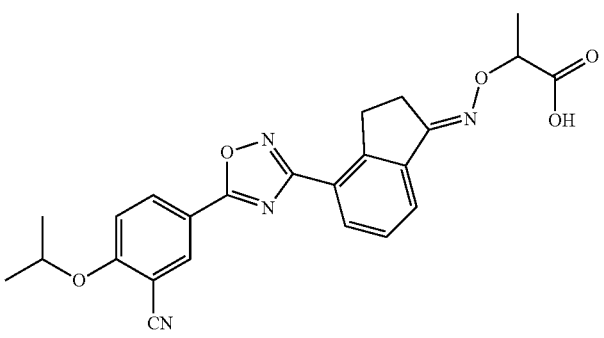 [SMILES: CC(C)Oc1ccc(-c2nc(-c3cccc4c3CC/C4=N\OC(C)C(=O)O)no2)cc1C#N] |
As mentions above, compounds having the structure of Formula (I) also include pharmaceutically acceptable salts, homologs, hydrates and solvents thereof.
A "salt" as is well known in the art includes an organic compound such as a carboxylic acid, a sulfonic acid, or an amine, in iconic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium and alkyl ammonium salts such as tromethamine salts, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present disclosure may take the form of salts. The term "salts" embraces addition salts of free acids or free bases which are compounds of the disclosure. Salts can be "pharmaceutically-acceptable salts." The term "pharmaceutically acceptable salt" refers to salts which possess toxicity profiles within a range that affords utility in pharmaceutical applications. Pharmaceutically unacceptable salts may nonetheless possess properties such as high crystallinity, which have utility in the practice of the present disclosure, such as for example utility in process of synthesis, purification or formulation of compounds of the disclosure.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4 hydroxybenzoic, phenylacetic, mandelic, embonic (pamoic), methanesulfonic, ethanesulfonic, benzenesulfonic, pantothenic, trifluoromethanesulfonic, 2 hydroxyethanesulfonic, p toluenesulfonic, sulfanilic, cyclohexylaminosulfonic, stearic, alginic, β hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the disclosure include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of compounds, for example in their purification by recrystallization. All of these salts may be prepared by conventional means from the corresponding compound by reacting, for example, the appropriate acid or base with the compound. The term "pharmaceutically acceptable salts" refers to nontoxic inorganic or organic acid and/or base addition salts, see, for example, Gould et al., Salt Selection for Basic Drugs (1986), *Int J. Pharm.*, 33, 201-217, incorporated by reference herein.

Non-limiting examples of potential salts of this disclosure include but are not limited to hydrochloride, citrate, glycolate, fumarate, malate, tartrate, mesylate, esylate, cinnamate, isethionate, sulfate, phosphate, diphosphate, nitrate, hydrobromide, hydroiodide, succinate, formate, acetate, dichloroacetate, lactate, p-toluenesulfonate, pamitate, pidolate, pamoate, salicylate, 4-aminosalicylate, benzoate, 4-acetamido benzoate, glutamate, aspartate, glycolate, adipate, alginate, ascorbate, besylate, camphorate, camphorsulfonate, camsylate, caprate, caproate, cyclamate, laurylsulfate, edisylate, gentisate, galactarate, gluceptate, gluconate, glucuronate, oxoglutarate, hippurate, lactobionate, malonate, maleate, mandalate, napsylate, napadisylate, oxalate, oleate, sebacate, stearate, succinate, thiocyanate, undecylenate, and xinafoate.

A "homolog" of a compound of the disclosure is a compound having one or more atoms of the compound replaced by an isotope of such atom. For example, homologs include compounds with deuterium in place of one or more hydrogen atoms of the compound such as compounds of the disclosure in which the methyl groups of the isopropoxy moiety of Formulas I-R and I-S are fully or partially deuterated (e.g., $(D_3C)_2CHO-$). Isotopic substitutions which may be made in the formation of homologs of the disclosure include non-radioactive (stable) atoms such as deuterium and carbon 13, as well as radioactive (unstable) atoms such as tritium, carbon 14, iodine 123, iodine 125, and the like.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

The compound disclosed herein can be prepared by techniques known to one skilled in the art, as well as by the procedures disclosed in the following Examples.

EXAMPLES

General Methods of Synthesis $^1$H NMR (400 MHz) and $^{13}$C NMR (100 MHz) were obtained in solution of deuteriochloroform ($CDCl_3$), deuteriomethanol ($CD_3OD$) or dimethyl sulfoxide—$D_6$ (DMSO). NMR spectra were processed using Mestrec 5.3.0 and 6.0.1. $^{13}$C NMR peaks that are bracketed are two rotomers of the same carbon. Mass spectra (LCMS) were obtained using an Agilent 1100/6110 HPLC system equipped with a Thompson ODS-A, 100 A, 5μ (50×4.6 mm) column using water with 0.1% formic acid as the mobile phase A, and acetonitrile with 0.1% formic acid as the mobile phase B. The gradient was 20-100% with mobile phase B over 2.5 min then held at 100% for 2.5 mins. The flow rate was 1 mL/min. For more hydrophobic compounds, the following gradient was used, denoted as Method 1: 40-95% over 0.5 min, hold at 95% for 8.5 min, then return to 40% over 2 min, with a flow rate of 1 mL/min. Final compounds were checked for purity using Method 2: 5% for 1 min, 5-95% over 9 min, then hold at 95% for 5 min, with a flow rate of 1 mL/min. Enantiomeric excess was determined by integration of peaks that were separated on a Chiralpak AD-H, 250×4.6 mm column, 5 μm particle size. Flow rate of 1 mL/min and an isocratic mobile phase. Unless otherwise indicated, the chiral data provided uses this method. Alternatively, chiral separations were performed under the following conditions, denoted as Chiral Method 1: Chiralpak AY-H, 250×4.6 mm column, 5 μm particle size. Flow rate of 1 mL/min and an isocratic mobile phase. Chiral Method 2: Chiralcel OZ-3, 250×4.6, 3 μm particle size at a flow rate of 0.75 ml/min. The pyridine, dichloromethane (DCM), tetrahydrofuran (THF), and toluene used in the procedures were from Aldrich Sure-Seal bottles kept under nitrogen ($N_2$). All reactions were stirred magnetically and temperatures are external reaction temperatures. Chromatographies were carried out using a Combiflash Rf flash purification system (Teledyne Isco) equipped with Redisep (Teledyne Isco) silica gel ($SiO_2$) columns. Preparative HPLC purifications were done on Varian ProStar/PrepStar system using water containing 0.05% trifluoroacetic acid as mobile phase A, and acetonitrile with 0.05% trifluoroacetic acid as mobile phase B. The gradient was 10-80% with mobile phase B over 12 min, hold at 80% for 2 min, and then return to 10% over 2 min with flow rate of 22 mL/min. Other methods similar to this may have been employed. Fractions were collected using a Varian Prostar fraction collector and were evaporated using a Savant SpeedVac Plus vacuum pump. Microwave heating was performed using a Biotage Initiator microwave reactor equipped with Biotage microwave vessels. The following abbreviations are used: ethanol (EtOH), carbonyldiimidazole (CDI), isopropanol (IPA), and 4-dimethylaminopyridine (DMAP).

Example 1

Synthesis of Compound No. 1

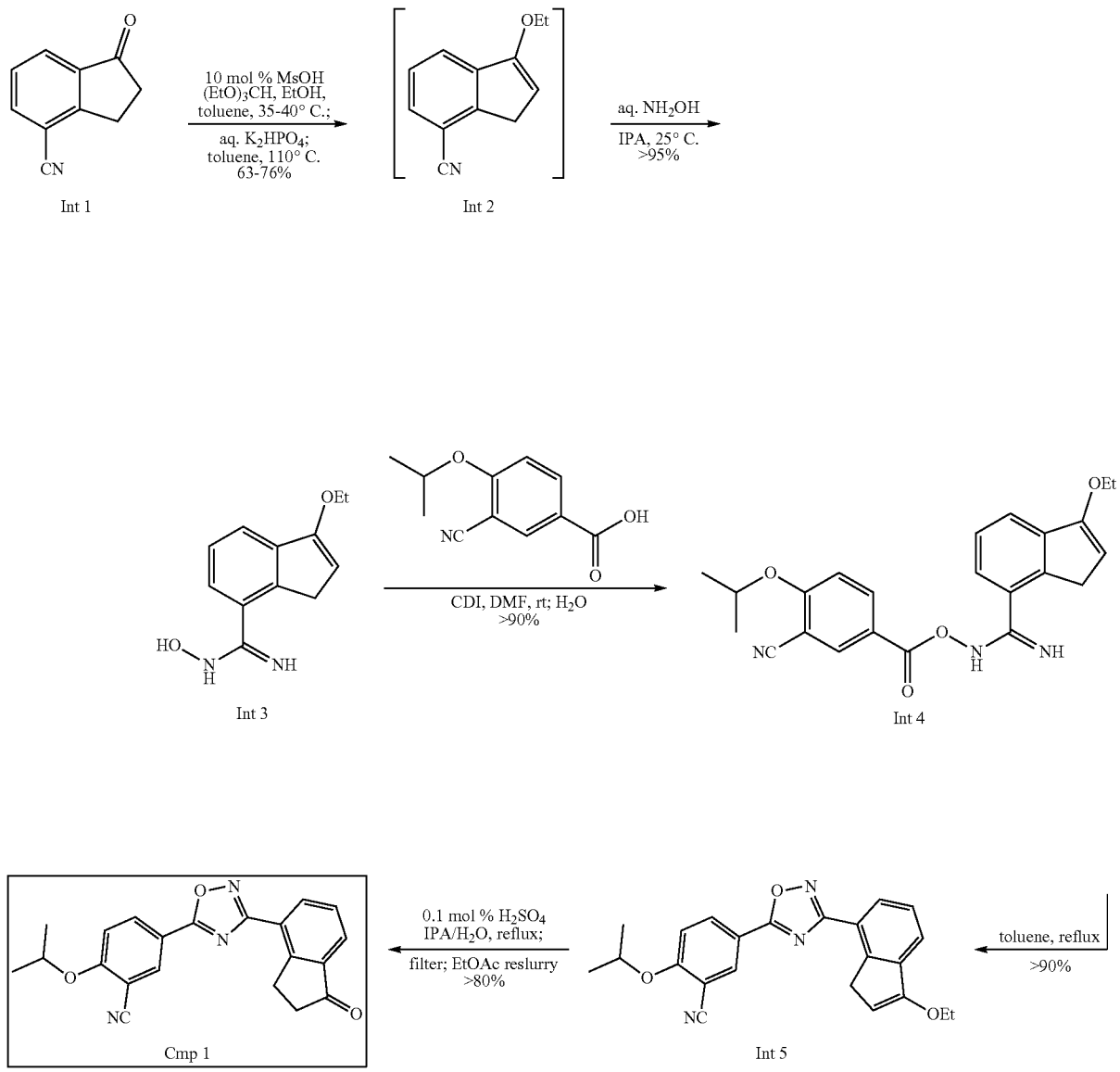

Step 1—Synthesis of 3-ethoxy-1H-indene-7-carbonitrile (Int 2)

A stirred mixture of 1-oxo-2,3-dihydro-1H-indene-4-carbonitrile (Int 1) (20.0 g, 98 wt %, 18.6 assay g, 124.8 mmol) in abs EtOH (20 mL), triethylorthoformate (80 mL, 481 mmol) and methanesulfonic acid (0.88 mL, 12.5 mmol) in toluene (80 mL) was heated at 43-47° C. After 1 h, GC analysis showed orthoformate consumed and 12.8 area % of Int 1 remaining. A further charge of triethylorthoformate (20 mL, 120.2 mmol) was made and after 45 min GC analysis showed 1.5 area % Int 1. The batch was cooled to ambient temperature and then poured into 1 M aq. $K_2HPO_4$ (200 mL) with vigorous stirring while maintaining a quench temperature <15° C. The two-phase mixture was vigorously stirred for 10 min. The phases were separated and the aqueous phase (pH 11) was back extracted with toluene (100 mL). The organic phases were combined and distilled at atmospheric pressure to remove 340 mL distillate. Toluene was added (500 mL) and distilled at atmospheric pressure to remove 500 mL distillate. Total distillation time 3 h, temperature range 80-120° C. At this point the batch was stored overnight at <5° C. Excess orthoformate was removed by chasing with ethyl acetate (100 mL) under reduced pressure until distillation stopped. Another volume of ethyl acetate (100 mL) was added and then concentrated under reduced pressure until distillation stopped. A third volume of ethyl acetate (100 mL) was added and then concentrated under reduced pressure until distillation stopped, after which GC analysis confirmed no orthoformate remaining. The crude was then stirred at 110° C. for 1 h, to convert the intermediate ketal to 3-ethoxy-1H-indene-7-carbonitrile (Int 2). Upon cooling, the crude (mobile oil, 21.34 g) was assayed for Int 2 by $^1$H NMR employing mesitylene as an internal standard. The oil assayed at 78.1 wt % product=16.73 assay g, 90.0 mmol=72.1% assay yield. The crude oil was then purified by filtration through a silica gel plug eluting with 15% EtOAc/hexane. The pure fractions were combined and utilized for the next step. $^1$H NMR (400 MHz, $d_6$-DMSO) δ 7.78 (d, J=8.4, 1H), 7.63 (m, 1H), 7.49 (m, 1H), 5.60 (m, 1H), 1.38 (t, J=6.8 Hz, 1H), 1.19 (t, J=6.8 Hz, 1H); LRMS: calcd for $C_{12}H_{12}NO^+$ [M+H]: 186.2; Found: 186.2.

Step 2—Synthesis of Int 3

An EtOAc/hexane solution (650 mL) of 3-ethoxy-1H-indene-7-carbonitrile (Int 2) is concentrated under reduced pressure to ~17 mL and isopropyl alcohol (IPA, 40 mL) was added. The solution was concentrated to ~17 mL, and a second volume of IPA (34 mL) was added. To the stirred solution was added aqueous hydroxylamine (50%, 30 mL, 455 mmol). The batch was then warmed at 35-40° C. for 5 h, and then stirred at ambient temperature overnight. The batch was cooled to 0° C., seeded (50 mg), and stirred for 30 min for a seed bed to develop. Water (250 mL) was then added dropwise over ~1.5 h. The batch was stirred for 1 h at 0-20° C. The product was isolated by filtration, cake-washed with water (100 mL) and dried on the filter under vacuum and a nitrogen atmosphere, to afford 3-ethoxy-N-hydroxy-1H-indene-7-carboximidamide (Int 3) (20.8 g, 90% yield). $^1$H NMR (400 MHz, $d_6$-DMSO) δ 9.61 (s, 1H), 7.43 (m, 1H), 7.32 (m, 2H), 5.77 (s, 1H), 5.41 (s, 1H), 4.08 (q, J=6.8 Hz, 2H), 3.45 (s, 2H), 1.39 (t, J=6.8 Hz, 3H); LRMS: calcd for $C_{12}H_{15}N_2O_2^+$ [M+H]: 219.2; Found: 219.1.

Step 3—Synthesis of N-((3-cyano-4-isopropoxybenzoyl)oxy)-3-ethoxy-1H-indene-7-carboximidamide (Int 4)

A mixture of CDI (16.64 g, 102.6 mmol) and 3-cyano-4-isopropoxyl benzoic acid (21.06 g 102.6 mmol) in DMF (83 mL) was stirred at 20° C. for 1 h. A solution of 3-ethoxy-N-hydroxy-1H-indene-7-carboximidamide (Int 3) (20.8 g, 93.3 mmol) in DMF (40 mL) was added through an addition funnel over ~5 min. After ~30 min the batch became viscous and a further volume of DMF (40 mL) was added to aid stirring. At this point HPLC assay indicated that the reaction was complete. The resulting slurry was diluted with water (1.5 L), cooled to 0° C., and isolated by filtration. The filter cake was washed with water (1.5 L) and the product dried on the filter under nitrogen flow to afford N-((3-cyano-4-isopropoxybenzoyl)oxy)-3-ethoxy-1H-indene-7-carboximidamide (Int 4) as an off white solid (34.8 g, 90% yield). $^1$H NMR (400 MHz, $d_6$-DMSO) δ 8.70 (s, 1H), 8.33 (d, J=6.8 Hz, 1H), 7.45 (m, 4H), 7.10 (m, 2H), 5.49 (s, 1H), 4.94 (m, 1H), 4.10 (q, J=6.8 Hz, 2H), 3.55 (s, 2H), 1.38 (m, 9H); LRMS: calcd for $C_{23}H_{24}N_3O_4^+$ [M+H]: 406.4; Found: 406.2.

Step 4—Synthesis of 5-(3-(3-ethoxy-1H-inden-7-yl)-1,2,4-oxadiazol-5-yl)-2-isopropoxybenzonitrile (Int 5)

N-((3-Cyano-4-isopropoxybenzoyl)oxy)-3-ethoxy-1H-indene-7-carboximidamide (Int 4) (34.8 g, 83.97 mmol) was suspended in toluene (590 mL) and heated to reflux with a Dean-Stark apparatus for 18 h. ~2 mL were collected (theory 1.5 mL). The batch was cooled to ambient temperature, filtered through Celite, and concentrated under vacuum. The crude solid 5-(3-(3-ethoxy-1H-inden-7-yl)-1,2,4-oxadiazol-5-yl)-2-isopropoxybenzonitrile (Int 5) (30 g, 90% yield) is taken as is to the next step. LRMS: calcd for $C_{23}H_{22}N_3O_3^+$ [M+H]: 388.4; Found: 388.3.

Step 5—Synthesis 2-isopropoxy-5-(3-(1-oxo-2,3-dihydro-1H-inden-4-yl)-1,2,4-oxadiazol-5-yl)benzonitrile (Cpd. No. 1)

Int 5 (30 g, 75.57 mmol) is suspended in 4:1 IPA/$H_2O$ (300 mL). Catalytic $H_2SO_4$ (0.1 mL, 0.19 mmol) is added, and the resulting mixture is heated to reflux for 12 h. The slurry is cooled to ambient temperature and stirred for 1 h. The product is isolated by filtration and washed with 4:1 IPA/$H_2O$ (100 mL). After drying on the filter for 1 h under vacuum, the wet cake is charged back to the reactor and suspended in EtOAc (300 mL). The mixture is heated to reflux for 3 h, then cooled to ambient temperature and stirred for 1 h. The slurry is filtered, washed with EtOAc (100 mL), and dried on the filter under nitrogen to afford 2-isopropoxy-5-(3-(1-oxo-2,3-dihydro-1H-inden-4-yl)-1,2,4-oxadiazol-5-yl)benzonitrile (Cpd. No. 1) (22 g, 80% yield) as an off-white solid. $^1$H NMR (400 MHz, $d_6$-DMSO) δ 8.55 (d, J=2.0 Hz, 1H), 8.44 (m, 2H), 7.88 (d, J=7.6 Hz, 1H), 7.69 (t, J=7.6 Hz, 1H), 7.57 (d, J=9.2 Hz, 1H), 4.99 (h, J 12.4 Hz, 1H), 3.46 (dd, $J_1$=5.6, $J_2$=11.2 Hz, 2H), 2.76 (dd, $J_1$=5.6, $J_2$=11.2 Hz, 2H), 1.45 (d, J=12.4 Hz, 6H); $^{13}$C NMR (100 MHz, $d_6$-DMSO) δ 205.9, 173.4, 167.4, 162.6, 154.2, 138.1, 134.7, 134.2, 133.9, 128.2, 125.9, 124.5, 115.8, 115.3, 114.9, 102.5, 72.6, 35.9, 27.3, 21.5; LRMS: calcd for $C_{21}H_{18}N_3O_3^+$ [M+H]: 360.1; Found: 360.2; C, H, N Analysis: Found: % C: 70.25, % H: 4.69; % N: 11.71; Theory: % C: 70.18; % H: 4.77; % N: 11.69.

Example 2

General Synthesis of Compounds of Formula (I)

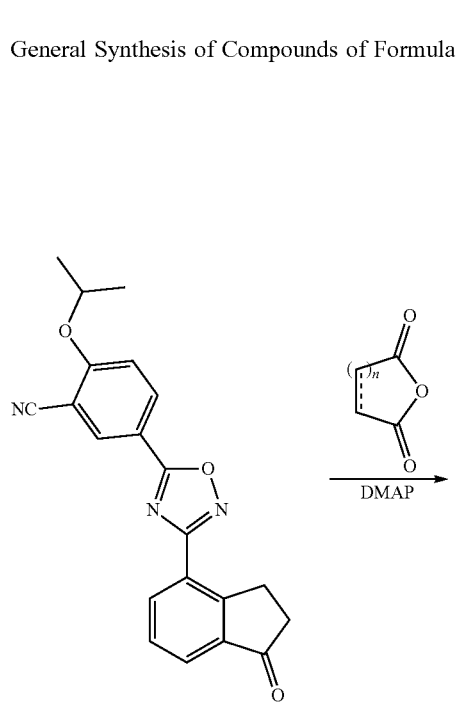

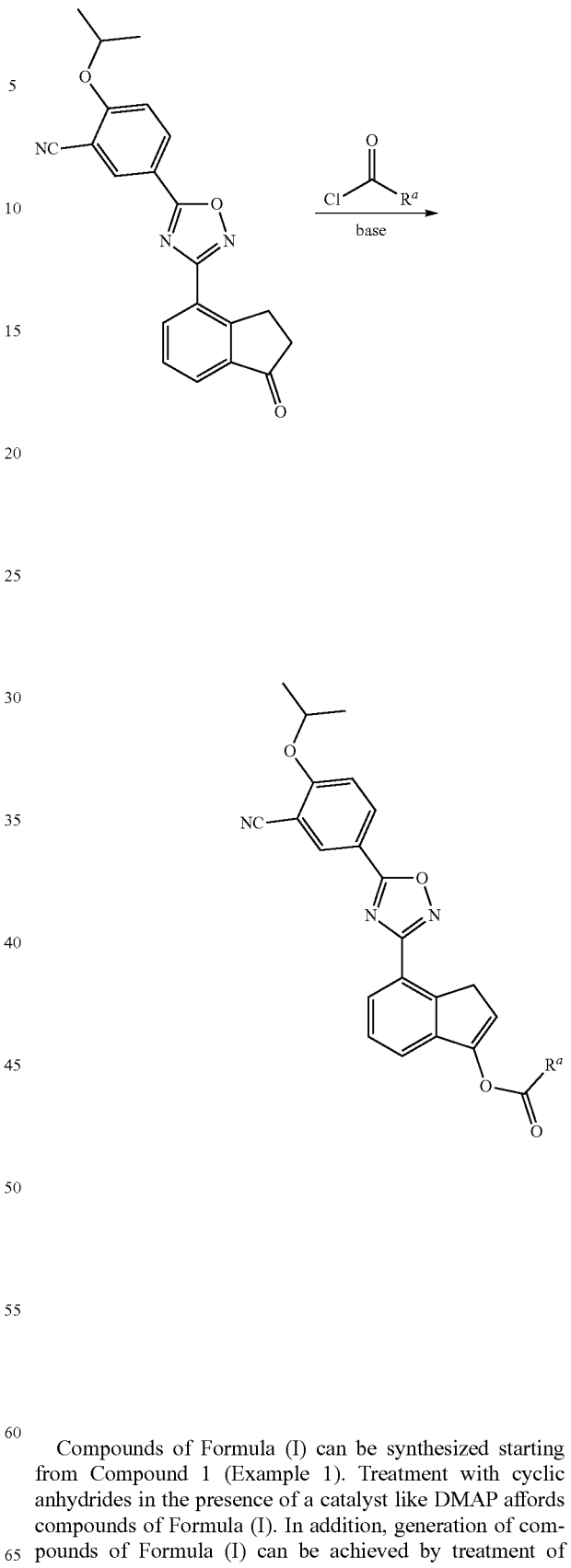

Compounds of Formula (I) can be synthesized starting from Compound 1 (Example 1). Treatment with cyclic anhydrides in the presence of a catalyst like DMAP affords compounds of Formula (I). In addition, generation of compounds of Formula (I) can be achieved by treatment of Compound 1 with a strong base followed by trapping with an acid chloride.

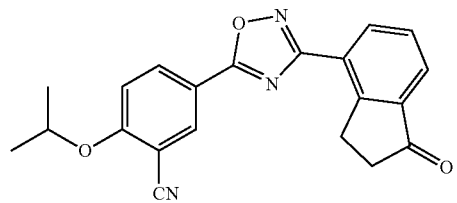 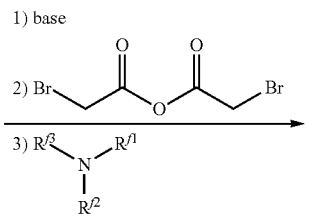

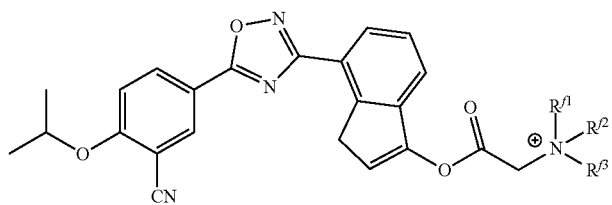

Compounds of Formula (I) can also be synthesized starting from Compound 1 (Example 1) by treatment with strong base followed by trapping with a 2-haloacetic anhydride and amination of the corresponding alpha haloester with a tertiary amine (wherein $R^{f1}$, $R^{f2}$ and $R^{f3}$ in the above scheme represents alkyl, such as $C_{1-4}$alkyl).

Example 3

Synthesis of Compound 10

((Z)-5-(3-(1-(hydroxyimino)-2,3-dihydro-1H-inden-4-yl)-1,2,4-oxadiazol-5-yl)-2-isopropoxybenzonitrile)

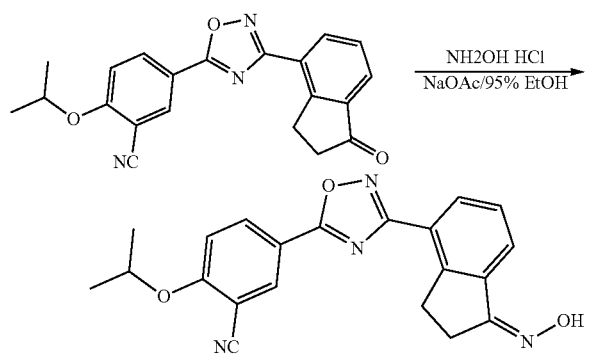

2-isopropoxy-5-(3-(1-oxo-2,3-dihydro-1H-inden-4-yl)-1,2,4-oxadiazol-5-yl)benzonitrile (100 mg, 0.28 mmol) in DCM (8 ml, complete dissolved) was added 95% EtOH (4 ml), $NH_2OH$ (43 mg, 0.61 mmol) and NaOAc (52 mg, 0.61 mmol) at rt. The progress of the reaction was monitored by HPLC. After the reaction was complete (overnight), the precipitated was collected and washed with DCM (5 ml×2) to give pure product: (Z)-5-(3-(1-(hydroxyimino)-2,3-dihydro-1H-inden-4-yl)-1,2,4-oxadiazol-5-yl)-2-isopropoxybenzonitrile (60 mg, 0.16 mmol, 57%). $^1$H NMR (400 MHz, DMSO-D6) δ ppm 1.40 (d, J=8 Hz, 6H), 2.90 (m, 2H), 3.39 (m, 2H), 4.99 (m, 1H), 7.56 (m, 2H), 7.80 (d, J=8 Hz, 1H), 8.14 (d, J=8 Hz, 1H), 8.42 (d, J=8 Hz, 1H), 8.54 (s, 1H), 11.1 (s, 1H); ESIMS found for $C_{21}H_{18}N_4O_3$: m/z 375.3 (M+1).

Example 4

Synthesis of Compound 11

((Z)-4-(((4-(5-(3-cyano-4-isopropoxyphenyl)-1,2,4-oxadiazol-3-yl)-2,3-dihydro-1H-inden-1-ylidene)amino)oxy)butanoic acid)

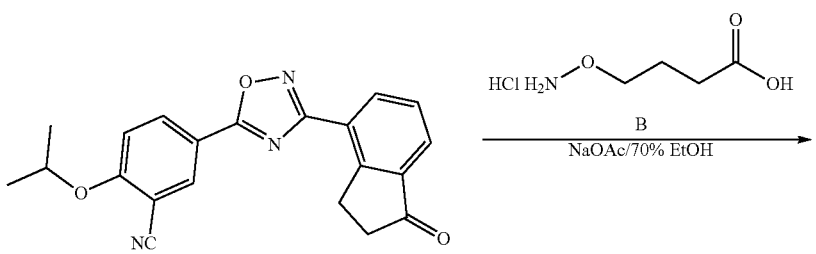

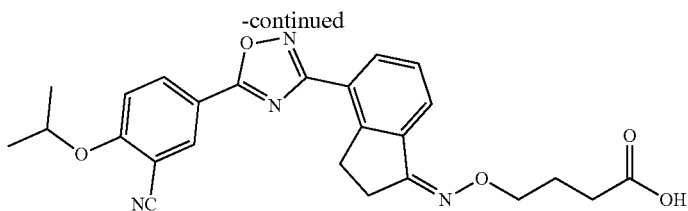

2-isopropoxy-5-(3-(1-oxo-2,3-dihydro-1H-inden-4-yl)-1,2,4-oxadiazol-5-yl)benzonitrile (100 mg, 0.28 mmol) in DCM (8 ml, complete dissolved) was added 70% EtOH (4 ml), 4-(aminooxy)butanoic acid hydrochloride (95 mg, 0.61 mmol) and NaOAc (68 mg, 0.61 mmol) at rt. The progress of the reaction was monitored by HPLC. The reaction was stirred for 48 h at room temperature yielding 30% conversion. Solvent was removed and directly load on ISCO for purification. However, it was not separated; so re-purified by RP ISCO [5-95% MeOH-(contained 0.05% AcOH)/water to provide desired product: (Z)-4-(((4-(5-(3-cyano-4-isopropoxyphenyl)-1,2,4-oxadiazol-3-yl)-2,3-dihydro-1H-inden-1-ylidene)amino)oxy)butanoic acid (19 mg, 0.041 mmol, 15%). $^1$H NMR (400 MHz, DMSO-D6) δ ppm 1.47 (d, J=8 Hz, 6H), 2.09 (m, 2H), 2.54 (m, 2H), 2.95 (m, 2H), 3.41 (m, 2H), 4.26 (m, 2H), 4.80 (m, 1H), 7.10 (d, J=8 Hz, 1H), 7.40 (m, 1H), 7.83 (d, J=8 Hz, 1H), 8.12 (d, J=8 Hz, 1H), 8.34 (d, J=8 Hz, 1H), 8.40 (s, 1H); ESIMS found for $C_{25}H_{24}N_4O_5$: m/z 461.3 (M+1).

Example 5

Synthesis of Compound 12

((Z)-4-(5-(3-((12-azaneylidene)-13-methyl)-4-isopropoxyphenyl)-1,2,4-oxadiazol-3-yl)-2,3-dihydro-1H-inden-1-one O-(3-(dimethylamino)propyl) oxime)

(Z)-4-(5-(3-((12-azaneylidene)-13-methyl)-4-isopropoxyphenyl)-1,2,4-oxadiazol-3-yl)-2,3-dihydro-1H-inden-1-one O-(3-(dimethylamino)propyl) oxime was prepared in accordance with the procedures described in Example 4, except 4-(aminooxy)butanoic acid hydrochloride was replaced by 3-(aminooxy)-N,N-dimethylpropan-1-amine in 25% yield. $^1$H NMR (400 MHz, CHLOROFORM-d) δ ppm 1.48 (d, J=8 Hz, 6H), 2.25 (m, 2H), 2.7 (s, 6H), 2.97 (m, 4H), 3.45 (m, 2H), 4.29 (m, 2H), 4.81 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{26}H_{29}N_5O_3$: m/z 460.5 (M+1).

Example 6

Synthesis of Compound 13

((Z)-4-(5-(3-((12-azaneylidene)-13-methyl)-4-isopropoxyphenyl)-1,2,4-oxadiazol-3-yl)-2,3-dihydro-1H-inden-1-one O-propionyl oxime)

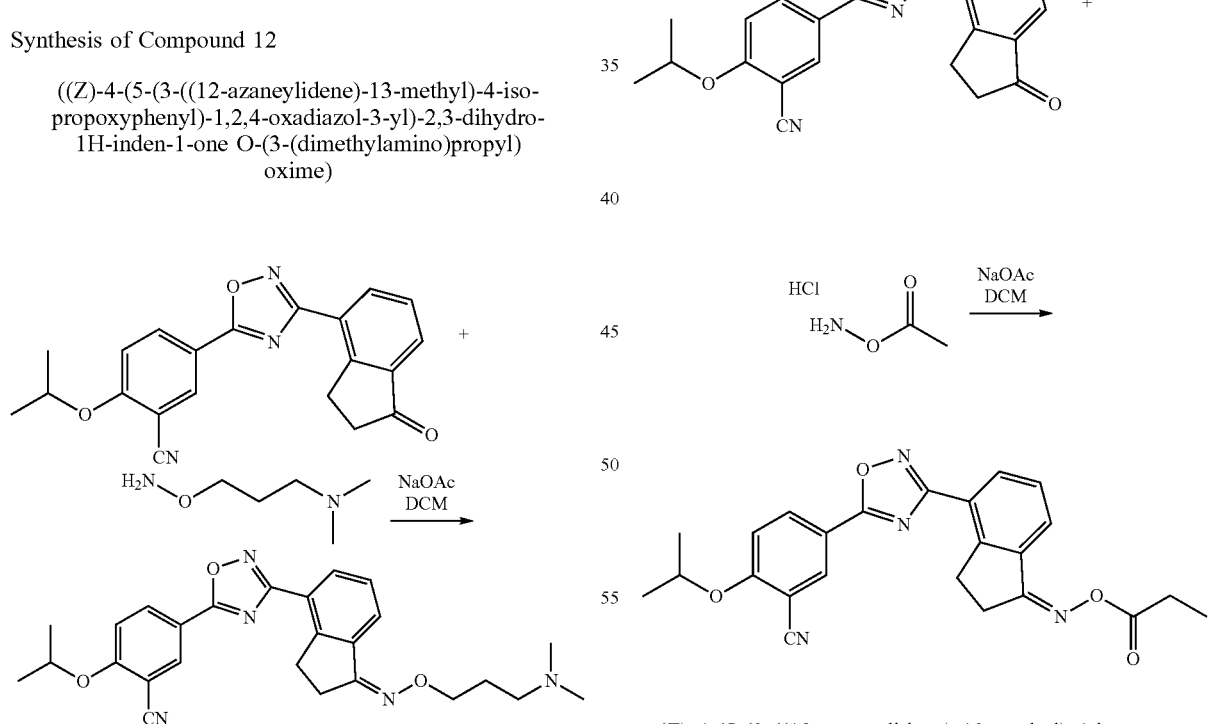

(Z)-4-(5-(3-((12-azaneylidene)-13-methyl)-4-isopropoxyphenyl)-1,2,4-oxadiazol-3-yl)-2,3-dihydro-1H-inden-1-one O-propionyl oxime was prepared in accordance with the procedures described in Example 4, except 4-(aminooxy)butanoic acid hydrochloride was replaced by O-propionylhydroxylamine hydrochloride in 3% yield. ESIMS found for $C_{24}H_{22}N_4O_4$: m/z 431.5 (M+1).

Example 7

Synthesis of Compound 14

((Z)-2-isopropoxy-5-(3-(1-((2-methoxyethoxy)imino)-2,3-dihydro-1H-inden-4-yl)-1,2,4-oxadiazol-5-yl)benzonitrile)

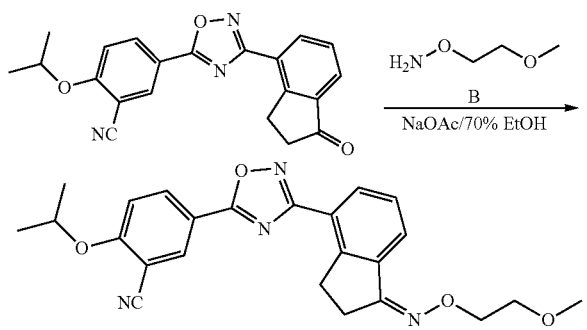

(Z)-2-isopropoxy-5-(3-(1-((2-methoxyethoxy)imino)-2,3-dihydro-1H-inden-4-yl)-1,2,4-oxadiazol-5-yl)benzonitrile was prepared in accordance with the procedures described in Example 4, except 4-(aminooxy)butanoic acid hydrochloride was replaced by O-(2-methoxyethyl)hydroxylamine in 7% yield. $^1$H NMR (400 MHz, CHLOROFORM-d) δ ppm 1.48 (d, J=8 Hz, 6H), 3.0 (m, 2H), 3.01 (s, 3H), 3.05 (m, 2H), 3.72 (m, 2H), 4.37 (m, 2H), 4.81 (m, 1H), 7.12 (d, J=8 Hz, 1H), 7.45 (t, J=4 Hz, 1H), 7.86 (d, J=8 Hz, 1H), 8.23 (d, J=8 Hz, 1H), 8.35 (d, J=8 Hz, 1H), 8.46 (s, 1H); ESIMS found for $C_{24}H_{24}N_4O_4$: m/z 433.2 (M+1).

Example 8

Synthesis of Compound 6

((Z)-2-(((4-(5-(3-cyano-4-isopropoxyphenyl)-1,2,4-oxadiazol-3-yl)-2,3-dihydro-1H-inden-1-ylidene)amino)oxy)acetic acid)

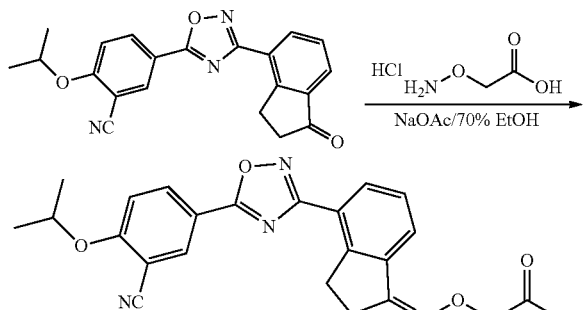

(Z)-2-(((4-(5-(3-cyano-4-isopropoxyphenyl)-1,2,4-oxadiazol-3-yl)-2,3-dihydro-1H-inden-1-ylidene)amino)oxy)acetic acid was prepared in accordance with the procedures described in Example 4, except 4-(aminooxy)butanoic acid hydrochloride was replaced by 2-(aminooxy)acetic acid hydrochloride in 42% yield. $^1$H NMR (400 MHz, DMSO-D6) δ ppm 1.47 (d, J=8 Hz, 6H), 2.92 (m, 2H), 3.29 (m, 2H), 4.62 (s, 2H), 4.80 (m, 1H), 7.48 (m, 2H), 7.71 (d, J=8 Hz, 1H), 8.11 (d, J=8 Hz, 1H), 8.31 (d, J=8 Hz, 1H), 8.40 (s, 1H); ESIMS found for $C_{23}H_{20}N_4O_5$: m/z 433.1 (M+1).

Example 9

Synthesis of Compound 15

((Z)-5-(3-(1-((2-(diethylamino)ethoxy)imino)-2,3-dihydro-1H-inden-4-yl)-1,2,4-oxadiazol-5-yl)-2-isopropoxybenzonitrile)

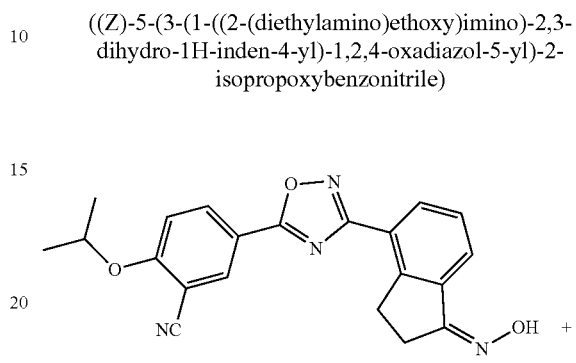

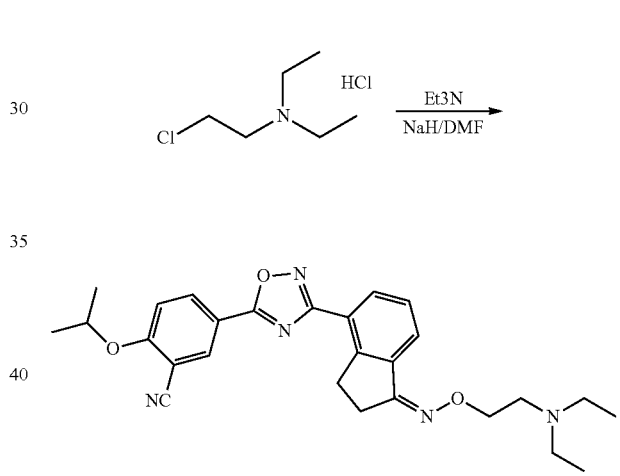

To 2-chloro-N,N-diethylethan-1-amine hydrochloride (138 mg, 0.8 mmol) in DMF (1.5 ml) was added Et$_3$N (0.112 ml, 0.8 mmol) and stirred at rt for 10 min. Meanwhile, to (Z)-5-(3-(1-(hydroxyimino)-2,3-dihydro-1H-inden-4-yl)-1,2,4-oxadiazol-5-yl)-2-isopropoxybenzonitrile (100 mg, 0.27 mmol) in DMF (1.5 ml) was added NaH (32 mg, 0.8 mmol, 60% in oil) at rt and stirred for 10 min. Then, the first solution was added to the second solution at rt and stirred overnight. The reaction mixture was poured into ice-water, extracted with DCM (20 ml), the DCM layer was washed with brine, dried, concentrated and purified by ISCO (eluting with 0-10% MeOH/DCM, 0.35M NH$_3$) to provide the desired product: (Z)-5-(3-(1-((2-(diethylamino)ethoxy)imino)-2,3-dihydro-1H-inden-4-yl)-1,2,4-oxadiazol-5-yl)-2-isopropoxybenzonitrile (23 mg, 0.048 mmol, 18%). $^1$H NMR (400 MHz, CHLOROFORM-d) δ ppm 1.07 (m, 6H), 1.47 (d, J=8 Hz, 6H), 2.66 (m, 4H), 2.99 (m, 4H), 3.42 (m, 2H), 4.31 (m, 2H), 4.81 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{27}H_{31}N_5O_3$: m/z 474.3 (M+H).

Example 10

Synthesis of Compound 9

((Z)-2-isopropoxy-5-(3-(1-((2-(piperidin-1-yl)ethoxy)imino)-2,3-dihydro-1H-inden-4-yl)-1,2,4-oxadiazol-5-yl)benzonitrile)

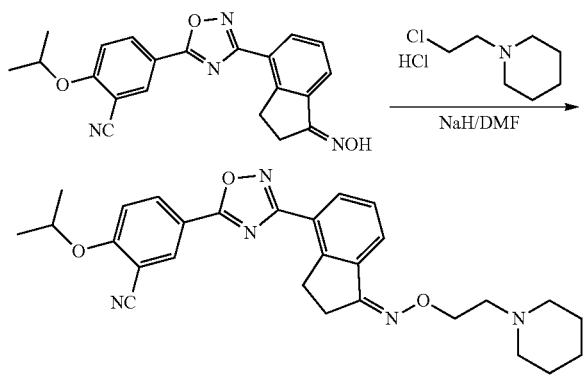

(Z)-2-isopropoxy-5-(3-(1-((2-(piperidin-1-yl)ethoxy)imino)-2,3-dihydro-1H-inden-4-yl)-1,2,4-oxadiazol-5-yl)benzonitrile was prepared in accordance with the procedures described in Example 9, except 2-chloro-N,N-diethylethan-1-amine hydrochloride was replaced by 1-(2-chloroethyl)piperidine hydrochloride in 37% yield. $^1$H NMR (400 MHz, CHLOROFORM-d) δ ppm 1.25 (m, 2H), 1.47 (d, J=8 Hz, 6H), 1.77 (m, 4H), 2.76 (m, 4H), 2.99 (m, 4H), 3.42 (m, 2H), 4.31 (m, 2H), 4.81 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{28}H_{31}N_5O_3$: m/z 486.5 (M+1).

Example 11

Synthesis of Compound 7

((E)-3-(((4-(5-(3-cyano-4-isopropoxyphenyl)-1,2,4-oxadiazol-3-yl)-2,3-dihydro-1H-inden-1-ylidene)amino)oxy)propanoic acid)

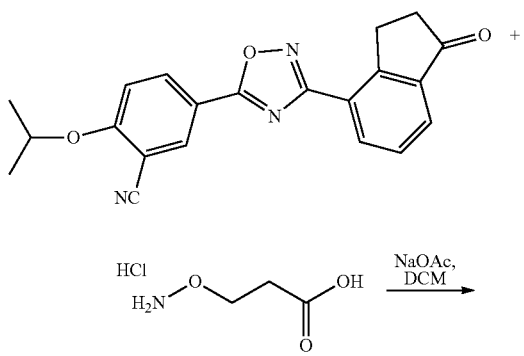

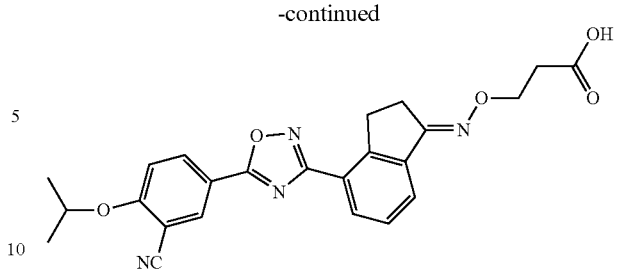

(E)-3-(((4-(5-(3-cyano-4-isopropoxyphenyl)-1,2,4-oxadiazol-3-yl)-2,3-dihydro-1H-inden-1-ylidene)amino)oxy)propanoic acid was prepared in accordance with the procedures described in Example 4, except 4-(aminooxy)butanoic acid hydrochloride was replaced by 3-(aminooxy)propanoic acid hydrochloride in 3% yield. $^1$H NMR (400 MHz, CHLOROFORM-d) δ ppm 1.47 (d, J=8 Hz, 6H), 2.86 (m, 2H), 2.97 (m, 2H), 3.46 (m, 2H), 4.48 (m, 2H), 4.81 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{24}H_{22}N_4O_5$: m/z 447.4 (M+1).

Example 12

Synthesis of Compound 2

((Z)-2-isopropoxy-5-(3-(1-(methoxyimino)-2,3-dihydro-1H-inden-4-yl)-1,2,4-oxadiazol-5-yl)benzonitrile)

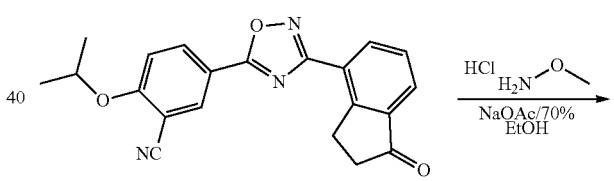

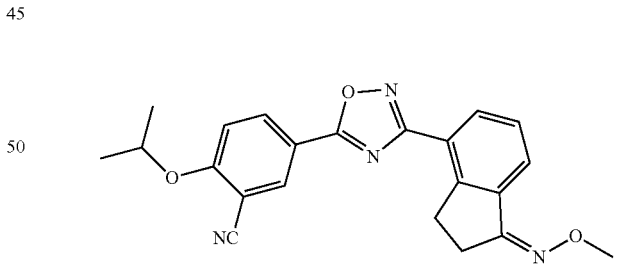

(Z)-2-isopropoxy-5-(3-(1-(methoxyimino)-2,3-dihydro-1H-inden-4-yl)-1,2,4-oxadiazol-5-yl)benzonitrile (N39-031) was prepared in accordance with the procedures described in Example 4, except 4-(aminooxy)butanoic acid hydrochloride was replaced by O-methylhydroxylamine hydrochloride in 34% yield. $^1$H NMR (400 MHz, CHLOROFORM-d) δ ppm 1.47 (d, J=8 Hz, 6H), 2.97 (m, 2H), 3.44 (m, 2H), 4.01 (s, 3H), 4.81 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{22}H_{20}N_4O_3$: m/z 389.1 (M+1).

Example 13

Synthesis of Compound 2

((Z)-5-(3-(1-(ethoxyimino)-2,3-dihydro-1H-inden-4-yl)-1,2,4-oxadiazol-5-yl)-2-isopropoxybenzonitrile)

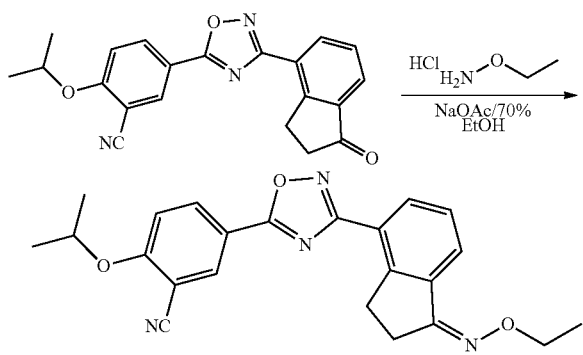

(Z)-5-(3-(1-(ethoxyimino)-2,3-dihydro-1H-inden-4-yl)-1,2,4-oxadiazol-5-yl)-2-isopropoxybenzonitrile (N39-030) was prepared in accordance with the procedures described in Example 4, except 4-(aminooxy)butanoic acid hydrochloride was replaced by O-ethylhydroxylamine hydrochloride in 65% yield. $^1$H NMR (400 MHz, CHLOROFORM-d) δ ppm 1.34 (m, 3H), 1.47 (d, J=8 Hz, 6H), 2.97 (m, 2H), 3.00 (m, 2H), 4.23 (m, 2H), 4.81 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{23}H_{22}N_4O_3$: m/z 402.4 (M+).

Example 14

Synthesis of Compound 4

((Z)-2-isopropoxy-5-(3-(1-(isopropoxyimino)-2,3-dihydro-1H-inden-4-yl)-1,2,4-oxadiazol-5-yl)benzonitrile)

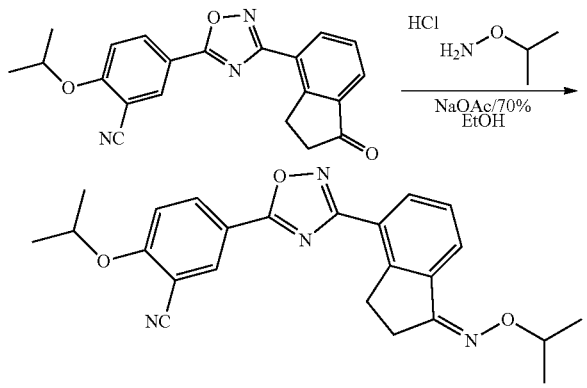

(Z)-2-isopropoxy-5-(3-(1-(isopropoxyimino)-2,3-dihydro-1H-inden-4-yl)-1,2,4-oxadiazol-5-yl)benzonitrile was prepared in accordance with the procedures described in Example 4, except 4-(aminooxy)butanoic acid hydrochloride was replaced by O-isopropylhydroxylamine hydrochloride in 48% yield. ESIMS found for $C_{24}H_{24}N_4O_3$: m/z 417.2 (M+1).

Example 15

Synthesis of Compound 5

((Z)-5-(3-(1-(tert-butoxyimino)-2,3-dihydro-1H-inden-4-yl)-1,2,4-oxadiazol-5-yl)-2-isopropoxybenzonitrile)

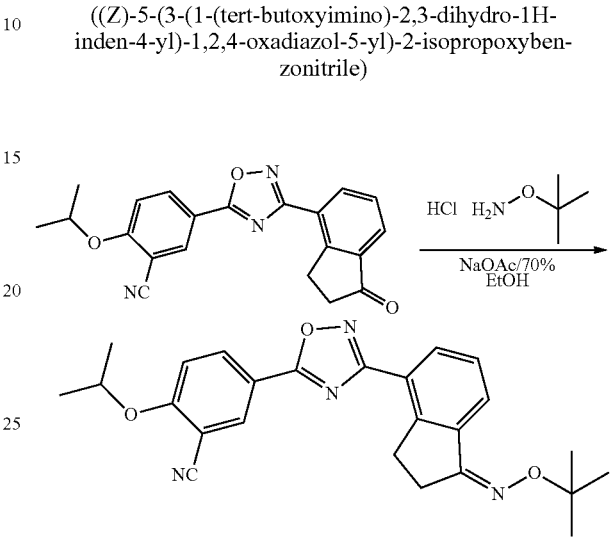

(Z)-5-(3-(1-(tert-butoxyimino)-2,3-dihydro-1H-inden-4-yl)-1,2,4-oxadiazol-5-yl)-2-isopropoxybenzonitrile was prepared in accordance with the procedures described in Example 4, except 4-(aminooxy)butanoic acid hydrochloride was replaced by O-(tert-butyl)hydroxylamine hydrochloride in 51% yield. $^1$H NMR (400 MHz, CHLOROFORM-d) δ ppm 1.36 (s, 9H), 1.47 (d, J=8 Hz, 6H), 2.97 (m, 2H), 3.44 (m, 2H), 4.81 (m, 1H), 7.12 (d, J=8 Hz, 1H), 7.45 (t, J=4 Hz, 1H), 7.80 (d, J=8 Hz, 1 H), 8.23 (d, J=8 Hz, 1H), 8.35 (d, J=8 Hz, 1H), 8.43 (s, 1H); ESIMS found for $C_{25}H_{26}N_4O_3$: m/z 431.2 (M+1).

Example 16

Synthesis of Compound 16

((Z)-5-(3-(1-((2-hydroxyethoxy)imino)-2,3-dihydro-1H-inden-4-yl)-1,2,4-oxadiazol-5-yl)-2-isopropoxybenzonitrile)

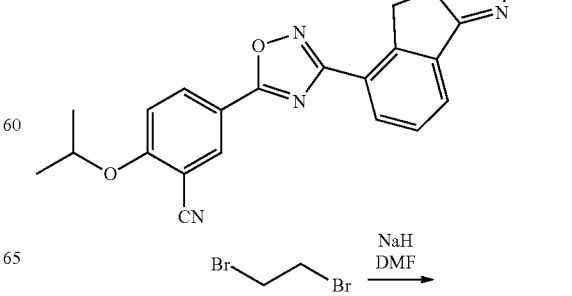

-continued

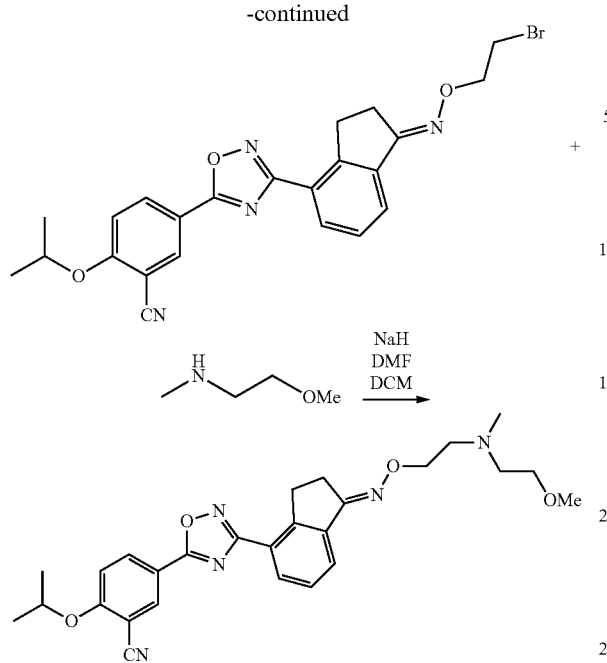

Step 1

A DMF (9 ml) solution of (E)-5-(3-(1-(hydroxyimino)-2,3-dihydro-1H-inden-4-yl)-1,2,4-oxadiazol-5-yl)-2-isopropoxybenzonitrile (0.6 g, 1.6 mmol) was added NaH (192 mg, 4.8 mmol) and stirred for 20 min. To the DMF slurry was added the DCM (6 ml) solution of 1,2-dibromoethane (3 g, 16 mmol). The reaction mixture was stirred at rt for 16 h. LCMS showed some conversion, the reaction mixture was diluted with DCM (100 mL) and washed with water (100 mL×2). The organic was dried over $Na_2SO_4$, concentrated and purified by ISCO (25 g column, 0-100% EtOAc/Hex) to give the desired product: (E)-5-(3-(1-((2-bromoethoxy)imino)-2,3-dihydro-1H-inden-4-yl)-1,2,4-oxadiazol-5-yl)-2-isopropoxybenzonitrile (0.08 g, 0.166 mmol, 10%). ESIMS found for $C_{23}H_{21}BrN_4O_3$: m/z 481.3 (M+1).

Step 2

To a 50 mL flask was added 2-methoxy-N-methylethan-1-amine (11 mg, 0.125 mmol), DMF (1 ml), NaH (5 mg, 0.125 mmol) and then stirred for 5 min. To the stirred mixture was added DCM (4 ml) solution of (E)-5-(3-(1-((2-bromoethoxy)imino)-2,3-dihydro-1H-inden-4-yl)-1,2,4-oxadiazol-5-yl)-2-isopropoxybenzonitrile (40 mg, 0.08 mmol) then stirred at rt for 16 h. The solvent was removed and the residue was purified by ISCO (4 g column, 0-10% MeOH/DCM, 0.35 N $NH_3$) to give the desired product: (E)-2-isopropoxy-5-(3-(1-((2-((2-methoxyethyl)(methyl)amino)ethoxy)imino)-2,3-dihydro-1H-inden-4-yl)-1,2,4-oxadiazol-5-yl)benzonitrile (10 mg, 0.02 mmol, 24%). $^1$H NMR (400 MHz, CHLOROFORM-d) δ ppm 1.47 (d, J=8 Hz, 6H), 2.49 (s, 3H), 2.50 (m, 2H), 2.80 (m, 2H), 2.99 (m, 2H), 3.40 (s, 3H), 3.46 (m, 2H), 3.50 (m, 2H), 4.36 (m, 2H), 4.80 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{27}H_{31}N_5O_4$: m/z 490.5 (M+1).

Example 17

Synthesis of Compound 17

((E)-5-(3-(1-((2-(azetidin-1-yl)ethoxy)imino)-2,3-dihydro-1H-inden-4-yl)-1,2,4-oxadiazol-5-yl)-2-isopropoxybenzonitrile)

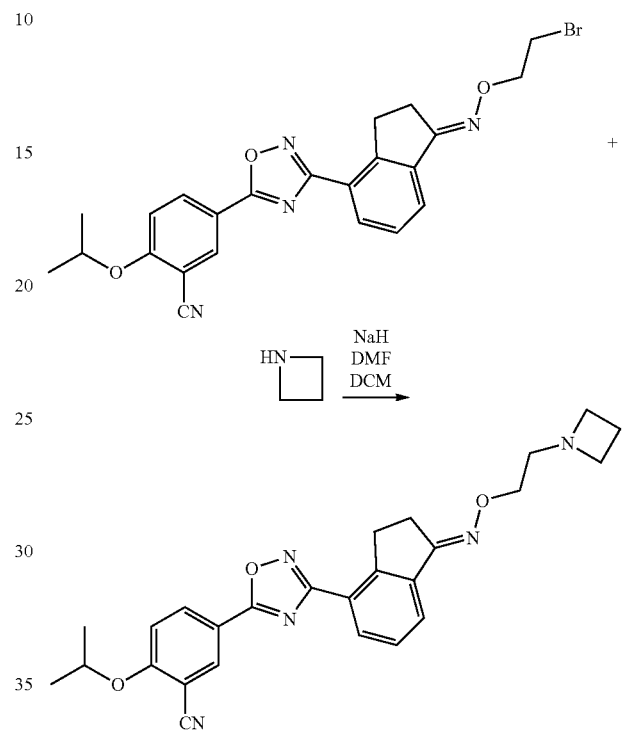

(E)-5-(3-(1-((2-(azetidin-1-yl)ethoxy)imino)-2,3-dihydro-1H-inden-4-yl)-1,2,4-oxadiazol-5-yl)-2-isopropoxybenzonitrile was prepared in accordance with the procedures described in Example 16 Step 2, except 2-methoxy-N-methylethan-1-amine was replaced by azetidine in 12.9% yield. $^1$H NMR (400 MHz, CHLOROFORM-d) δ ppm 1.47 (d, J=8 Hz, 6H), 1.82 (m, 2H), 2.46 (m, 2H), 2.90 (m, 2H), 3.01 (m, 2H), 3.46 (m, 2H), 3.60 (m, 2H), 4.36 (m, 2H), 4.80 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{26}H_{27}N_5O_3$: m/z 458.6 (M+1).

Example 18

Synthesis of Compound 18

((Z)-2-(((4-(5-(3-cyano-4-isopropoxyphenyl)-1,2,4-oxadiazol-3-yl)-2,3-dihydro-1H-inden-1-ylidene)amino)oxy)acetamide)

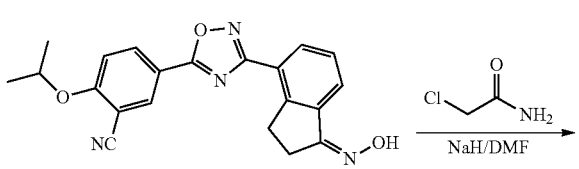

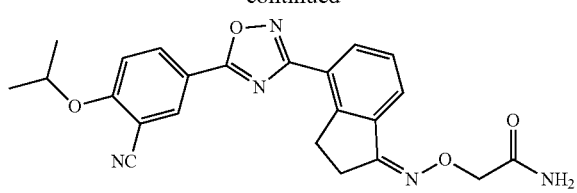

(Z)-2-(((4-(5-(3-cyano-4-isopropoxyphenyl)-1,2,4-oxadiazol-3-yl)-2,3-dihydro-1H-inden-1-ylidene)amino)oxy)acetamide was prepared in accordance with the procedures described in Example 9, except 2-chloro-N,N-diethylethan-1-amine hydrochloride was replaced by 2-chloroacetamide in 19.4% yield. $^1$H NMR (400 MHz, CHLOROFORM-d) δ ppm 1.47 (d, J=8 Hz, 6H), 3.00 (m, 2H), 3.5 (m, 2H), 4.69 (s, 2H), 4.78 (m, 1H), 5.50 (s, 1H), 6.40 (s, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{23}H_{21}N_5O_4$: m/z 432.4 (M+1).

Example 19

Synthesis of Compound 19

((E)-2-(((4-(5-(3-cyano-4-isopropoxyphenyl)-1,2,4-oxadiazol-3-yl)-2,3-dihydro-1H-inden-1-ylidene)amino)oxy)propanoic acid)

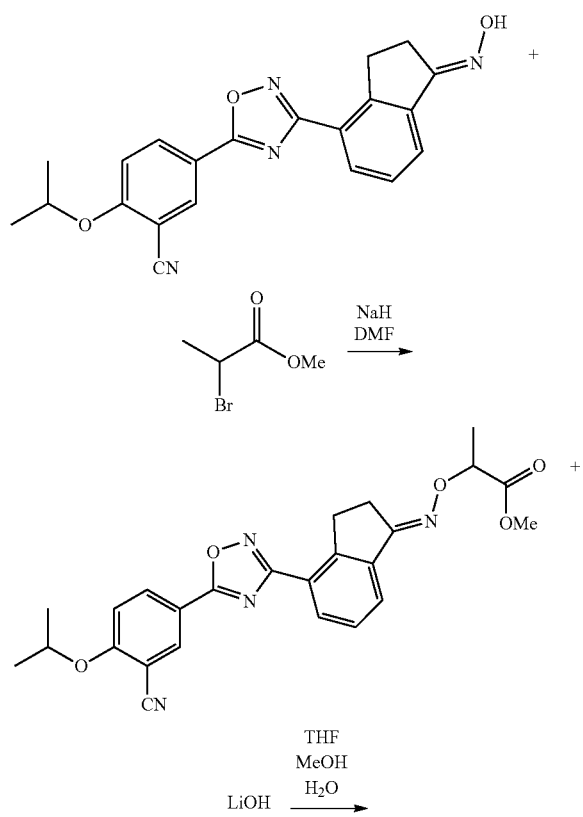

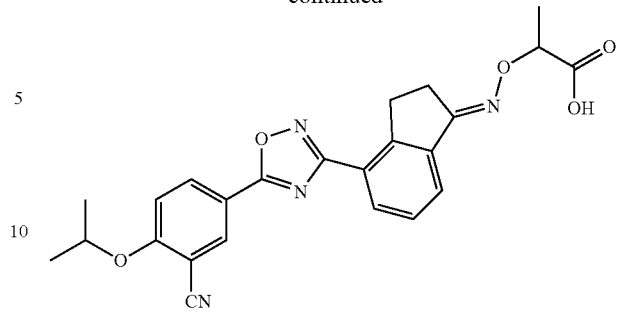

Step 1

Methyl (E)-2-(((4-(5-(3-cyano-4-isopropoxyphenyl)-1,2,4-oxadiazol-3-yl)-2,3-dihydro-1H-inden-1-ylidene)amino)oxy)propanoate was prepared in accordance with the procedures described in Example 9, except 2-chloro-N,N-diethylethan-1-amine hydrochloride was replaced by methyl 2-bromopropanoate in 80% yield. ESIMS found for $C_{25}H_{24}N_4O_5$: m/z 461.4 (M+1).

Step 2

A stirred solution of methyl (E)-2-(((4-(5-(3-cyano-4-isopropoxyphenyl)-1,2,4-oxadiazol-3-yl)-2,3-dihydro-1H-inden-1-ylidene)amino)oxy)propanoate (33 mg, 0.072 mmol) in THF (5 mL) and MeOH (2 mL) was treated with LiOH (10.3 mg, 0.215 mmol) aqueous solution (1 mL). The mixture was stirred at rt for 2 h. Then the mixture was acidified with 6M HCl to pH1. The mixture was diluted with DCM (20 mL) and extracted with water (20 mL). The aqueous layer was extracted with DCM (20 mL×3). The organics were combined, dried over $Na_2SO_4$ and then concentrated to give desire product: (E)-2-(((4-(5-(3-cyano-4-isopropoxyphenyl)-1,2,4-oxadiazol-3-yl)-2,3-dihydro-1H-inden-1-ylidene)-amino)oxy)propanoic acid (26 mg, 0.058 mmol, 81%). $^1$H NMR (400 MHz, CHLOROFORM-d) δ ppm 1.47 (d, J=8 Hz, 6H), 1.43 (s, 1H), 1.63 (d, J=8 Hz, 3H), 3.07 (m, 2H), 3.50 (m, 2H), 4.80 (m, 1H), 4.82 (m, 1H), 7.12 (d, J=8 Hz, 1H), 7.45 (t, J=4 Hz, 1H), 7.80 (d, J=8 Hz, 1H), 8.23 (d, J=8 Hz, 1H), 8.35 (d, J=8 Hz, 1H), 8.43 (s, 1H); ESIMS found for $C_{24}H_{22}N_4O_5$: m/z 447.4 (M+1).

Example 20

In Vitro Biological Assays

Cell Membrane Preparations

CHO cells expressing recombinant S1P receptors were cultured 500 cm$^2$ culture trays and once confluent, rinsed and detached with cell-lifting buffer (10 mM HEPES, 154 mM NaCl, 6.85 mM EDTA, pH 7.4). Cells were then pelleted by centrifugation, resuspended, and homogenized in membrane preparation buffer (10 mM HEPES and 10 mM EDTA, pH 7.4) using a Polytron PT 1200E homogenizer (Kinematica, Luzern, Switzerland). Cellular proteins were pelleted by centrifugation at 48,000×g at 4° C. for 30 minutes. The resulting supernatant was discarded, and the pellet was re-suspended again in membrane preparation buffer, homogenized for a second time and then centrifuged again as described above. The final cellular protein pellet was suspended in ice cold resuspension buffer (10 mM HEPES and 0.1 mM EDTA, pH 7.4), divided into aliquots, and stored at −80° C. until use.

GTPγS Binding Assay

Binding assays for [$^{35}$S]-GTPγS were performed in 96-well non-binding surface plates with a final volume of 200 μL. The test compounds were serial diluted in DMSO and added to assay plates using a Tecan D300E digital printer with a total volume of 0.4 µL. The control sphingosine-1-phosphate (S1P) was prepared separately by preparing a 400 µM stock solution from a 100 nmol pellet of S1P in 10 mM $Na_2CO_3$ with 2% β-cyclodextrin. The serial dilution of S1P was done using complete assay buffer (20 mM HEPES, 10 mM $MgCl_2$, 100 mM NaCl, 1 mM EDTA, 0.1% fatty acid free bovine serum albumin [BSA], and 30 µg/mL saponin, pH7.4) and transferred to wells already containing 0.4 µL DMSO. All the wells were then loaded to a total volume of 40 µL of complete assay buffer, except the non-specific binding (NSB) wells. For NSB wells, 40 L/well of 50 µM GTPγS (Sigma Aldrich, cat #G8634, St. Louis, MO) was added to wells containing 0.4 µL of DMSO. The assay was started by the addition of 120 µL/well of CHO—S1P receptor membrane solution containing 40 µg/mL of membrane protein, 16.67 µM guanosine diphosphate (GDP; Sigma Aldrich, cat #G7127, St. Louis, MO), and 2.5 mg/mL of WGA PVT SPA beads in complete buffer. Assay plates were then sealed and incubated at room temperature with gentle agitation for 30 minutes. Next, 40 µL/well of 1 nM of [$^{35}$S]-GTPγS (PerkinElmer, cat #NEG030X250UC, Waltham, MA) in basic assay buffer (20 mM HEPES, 10 mM $MgCl_2$, 100 mM NaCl, and 1 mM EDTA, pH7.4) was added to the assay plates to yield a final concentration of 200 µM and the plates were further incubated for 40 minutes at room temperature with gentle agitation. The assay was terminated by centrifugation of the plates at 1000 rpm for 3 minutes using an Eppendorf 5810R centrifuge (Eppendorf, Hamburg, Germany) and G protein bound radioactivity was quantitated using a MicroBeta2 microplate scintillation counter (PerkinElmer, Waltham, MA).

The data for representative compounds assayed by the above techniques are presented in Table 2.

TABLE 2

| Cpd. No. e | $S_1P_1$ | | $S_1P_5$ | |
|---|---|---|---|---|
| | $EC_{50}$ (uM) | % Efficacy | $EC_{50}$ (uM) | % Efficacy |
| 5 | 0.020 | 98 | 0.078 | 79 |
| 6 | 0.019 | 90 | >2.0 | — |
| 7 | 0.336 | 89 | 0.030 | 29 |
| 8 | 0.008 | 90 | 0.015 | 64 |
| 10 | 0.004 | 97 | 0.006 | 58 |
| 11 | 0.006 | 85 | 0.080 | 85 |

Example 21

In Vivo Biological Assays
Determination of Absolute Oral Bioavailability in Rats.

Pharmacokinetic studies are conducted in non-fasted male Sprague-Dawely rats (Simonsen Laboratories or Harlan Laboratories). Rats are housed in an ALAAC accredited facility and the research approved by the facilities Institutional Animal Care and Use Committee (IACUC). The animals are acclimated to the laboratory for at least 48 h prior to initiation of experiments.

Compounds are formulated in 5% DMSO/5% Tween20 and 90% purified water (intravenous infusion) or 5% DMSO/5% Tween20 and 90% 0.1N HCL (oral gavage). The concentration of the dosing solutions is verified by HPLC-UV. For intravenous dosing, compounds were administered by an infusion pump into the jugular vein over one minute to manually restrained animals (n=4 rats/compound). Oral dosing is by gavage using a standard stainless steel gavage needle (n=2-4 rats/compound). For both routes of administration, blood is collected at eight time-points after dosing with the final sample drawn 24 h post dose. Aliquots of the blood samples are transferred to polypropylene 96-well plate and frozen at −20° C. until analysis.

After thawing the blood samples at room temperature, 5 µL of DMSO is added to each well. Proteins are precipitated by adding 150 µL acetonitrile containing 200 nM internal standard (4-hydroxy-3-(alpha-iminobenzyl)-1-methyl-6-phenylpyrindin-2-(1H)-one) and 0.1% formic acid. Plates are mixed for 1 min on a plate shaker to facilitate protein precipitation and then centrifuged at 3,000 rpm for 10 min to pellet protein. The supernatant is transferred to a clean plate and centrifuged at 3,000 rpm for 10 min to pellet any remaining solid material prior to LC/MS/MS analysis. Calibration curve standards are prepared by spiking 5 µL compound stock in DMSO into freshly collected EDTA rat blood. An eight point standard curve spanning a range of 5 nM to 10,000 nM is included with each bio-analytical run. The standards are processed identically to the rat pharmacokinetic samples.

Concentrations in the rat pharmacokinetic samples are determined using a standardized HPLC-LC/MS/MS method relative to the eight point standard curve. The system consists of a Leap CTC Pal injector, Agilent 1200 HPLC with binary pump coupled with an Applied Biosystems 3200 QTrap. Compounds are chromatographed on a Phenomenex Synergy Fusion RP 20×2 mm 2 um Mercury Cartridge with Security Guard. A gradient method is used with mobile phase A consisting of 0.1% formic acid in water and mobile phase B consisting of 0.1% formic acid in acetonitrile at flow rates varying from 0.7 to 0.8 mL/min. Ions are generated in positive ionization mode using an electrospray ionization (ESI) interface. Multiple reaction monitoring (MRM) methods are developed specific to each compound. The heated nebulizer is set at 325° C. with a nebulizer current of 4.8 µA. Collision energies are used to generate daughter ions ranged between 29 and 39 V. Peak area ratios are obtained from MRM of the mass transitions specific for each compound used for quantification. The limit of quantification of the method is typically 5 nM. Data are collected and analyzed using Analyst software version 1.4.2.

Blood concentration versus time data are analyzed using non-compartmental methods (WinNonlin version 5.2; model 200 for oral dosing and model 202 for intravenous infusion). Absolute oral bioavailability (%) is calculated using the following expression: (Oral AUC×IV Dose)/(IV AUC×Oral Dose)×100.

Lymphopenia

In mice: Female C57BL6 mice (Simonsen Laboratories, Gilroy CA) are housed in an ALAAC accredited facility and the research was approved by the facilities Institutional Animal Care and Use Committee (IACUC). The animals are acclimated to the laboratory for at least 5 days prior to initiation of experiments. Mice (n=3/compound/time-point) are dosed by oral gavage with 1-30 mg/kg compound formulated in a vehicle consisting of 5% DMSO/5% Tween 20 and 90% 0.1N HCl. Control mice are dosed PO with the vehicle. Terminal whole blood samples are collected from isoflurane anesthetized mice by cardiac puncture into EDTA. Whole blood is incubated with rat anti-mouse CD16/CD32 (Mouse BD Fc Block, #553141), PE-Rat anti-mouse CD45R/B220 (BD #553089), APC-Cy7-Rat anti-mouse CD8a (BD #557654), and Alexa Fluor647-Rat anti-mouse CD4 (BD #557681) for 30 min on ice. Red blood cells are lysed using BD Pharm Lyse Lysing buffer (#555899) and white blood cells were analyzed by FACS. Lymphopenia is expressed as the % of white blood cells that were CD4 or CD8 positive T cells. The overall lymphopenia response over 24 h is estimated by calculating the area under the effect curve (AUEC) using the linear trapezoidal rule.

In rats: Male rats (Simonsen Laboratories, Gilroy CA) are housed in an ALAAC accredited facility and the research was approved by the facilities Institutional Animal Care and Use Committee (IACUC). The animals are acclimated to the laboratory for at least 5 days prior to initiation of experiments. Rats (n=3/compound/time-point) are dosed by oral gavage with 1-30 mg/kg compound formulated in a vehicle consisting of 5% DMSO/5% Tween 20 and 90% 0.1N HCL. Control rats are dosed PO with the vehicle. Whole blood is collected from isoflurane anesthetized rats via the retroorbital sinus and terminal samples were collected by cardiac puncture into EDTA. Whole blood is incubated with mouse anti-rat CD32 (BD #550271), PE-mouse anti-rat CD45R/B220 (BD #554881), PECy5-mouse anti-rat CD4 (BD #554839), and APC-mouse anti-rat CD8a (eBioscience #17-0084) for 30 minutes on ice. Red blood cells are lysed using BD Pharm Lyse Lysing buffer (#555899) and white blood cells are analyzed with a BD FACSArray. Lymphopenia is expressed as the % of white blood cells that were CD4 or CD8 positive T cells. The overall lymphopenia response over 24 h is estimated by calculating the area under the effect curve (AUEC) using the linear trapezoidal rule.

Lymphopenia

In mice: Female C57BL6 mice (Simonsen Laboratories, Gilroy CA) are housed in an ALAAC accredited facility and the research was approved by the facilities Institutional Animal Care and Use Committee (IACUC). The animals are acclimated to the laboratory for at least 5 days prior to initiation of experiments. Mice (n=3/compound/time-point) are dosed by oral gavage with 1 mg/kg compound formulated in a vehicle consisting of 5% DMSO/5% Tween 20 and 90% 0.1N HCl. Control mice are dosed PO with the vehicle. Terminal whole blood samples are collected from isoflurane anesthetized mice by cardiac puncture into EDTA. Whole blood is incubated with rat anti-mouse CD16/CD32 (Mouse BD Fc Block, #553141), PE-Rat anti-mouse CD45R/B220 (BD #553089), APC-Cy7-Rat anti-mouse CD8a (BD #557654), and Alexa Fluor647-Rat anti-mouse CD4 (BD #557681) for 30 min on ice. Red blood cells are lysed using BD Pharm Lyse Lysing buffer (#555899) and white blood cells were analyzed by FACS. Lymphopenia is expressed as the % of white blood cells that were CD4 or CD8 positive T cells. The overall lymphopenia response over 24 h is estimated by calculating the area under the effect curve (AUEC) using the linear trapezoidal rule.

In rats: Female rats (Simonsen Laboratories, Gilroy CA) are housed in an ALAAC accredited facility and the research was approved by the facilities Institutional Animal Care and Use Committee (IACUC). The animals are acclimated to the laboratory for at least 5 days prior to initiation of experiments. Rats (n=3/compound/time-point) are dosed by oral gavage with 1 mg/kg compound formulated in a vehicle consisting of 5% DMSO/5% Tween 20 and 90% 0.1N HCL. Control rats are dosed PO with the vehicle. Whole blood is collected from isoflurane anesthetized rats via the retroorbital sinus and terminal samples were collected by cardiac puncture into EDTA. Whole blood is incubated with mouse anti-rat CD32 (BD #550271), PE-mouse anti-rat CD45R/B220 (BD #554881), PECy5-mouse anti-rat CD4 (BD #554839), and APC-mouse anti-rat CD8a (eBioscience #17-0084) for 30 minutes on ice. Red blood cells are lysed using BD Pharm Lyse Lysing buffer (#555899) and white blood cells are analyzed with a BD FACS Array. Lymphopenia is expressed as the % of white blood cells that were CD4 or CD8 positive T cells. The overall lymphopenia response over 24 h is estimated by calculating the area under the effect curve (AUEC) using the linear trapezoidal rule.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. U.S. Provisional Application 63/001,073, filed Mar. 27, 2020 and U.S. Provisional Application 63/018,327, filed Apr. 30, 2020 are incorporated herein by reference, in their entirety.

We claim:

1. A compound having the structure of Formula (I):

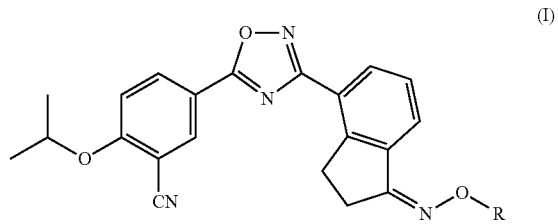

or a pharmaceutically acceptable salt, isotope, hydrate or solvate thereof, wherein:

R is:
 alkyl;
 alkanediyl-NR$^1$R$^2$;
 alkanediyl-C(=O)OR$^1$; or
 heterocyclylalkyl; and R$^1$ and R$^2$ are independently H or C$_{1-4}$alkyl.

2. The compound of claim 1 wherein R is alkyl.

3. The compound of claim 2 wherein alkyl is methyl, ethyl, isopropyl or tert-butyl.

4. The compound of claim 1 wherein R is alkanediyl-NR$^1$R$^2$.

5. The compound of claim 4 wherein R$^1$ and R$^2$ are independently hydrogen or methyl.

6. The compound of claim 1 wherein R is alkanediyl-C(=O)OR$^1$.

7. The compound of claim 6 wherein R$^1$ is hydrogen or methyl.

8. The compound of claim 1 wherein R is heterocyclylalkyl.

9. The compound of claim 8 wherein heterocyclealkyl is —(CH$_2$)-heterocycle.

10. The compound of claim 1 wherein the compound has one of the following structures, or a pharmaceutically acceptable salt, isotope, hydrate or solvate thereof:

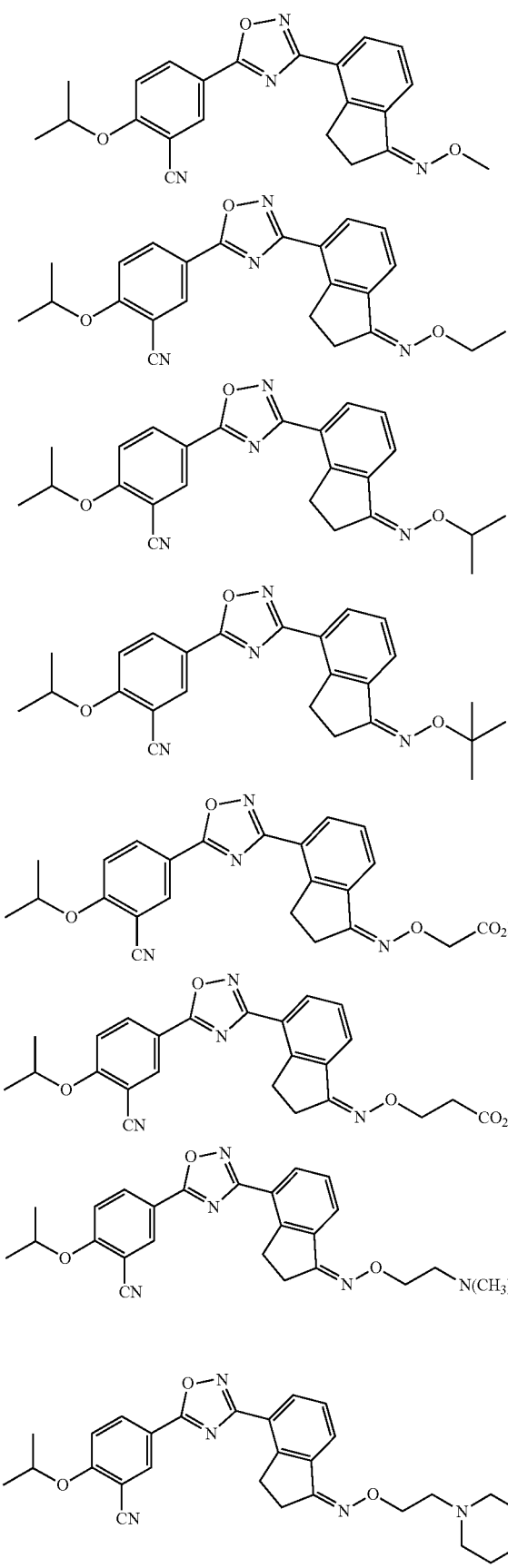
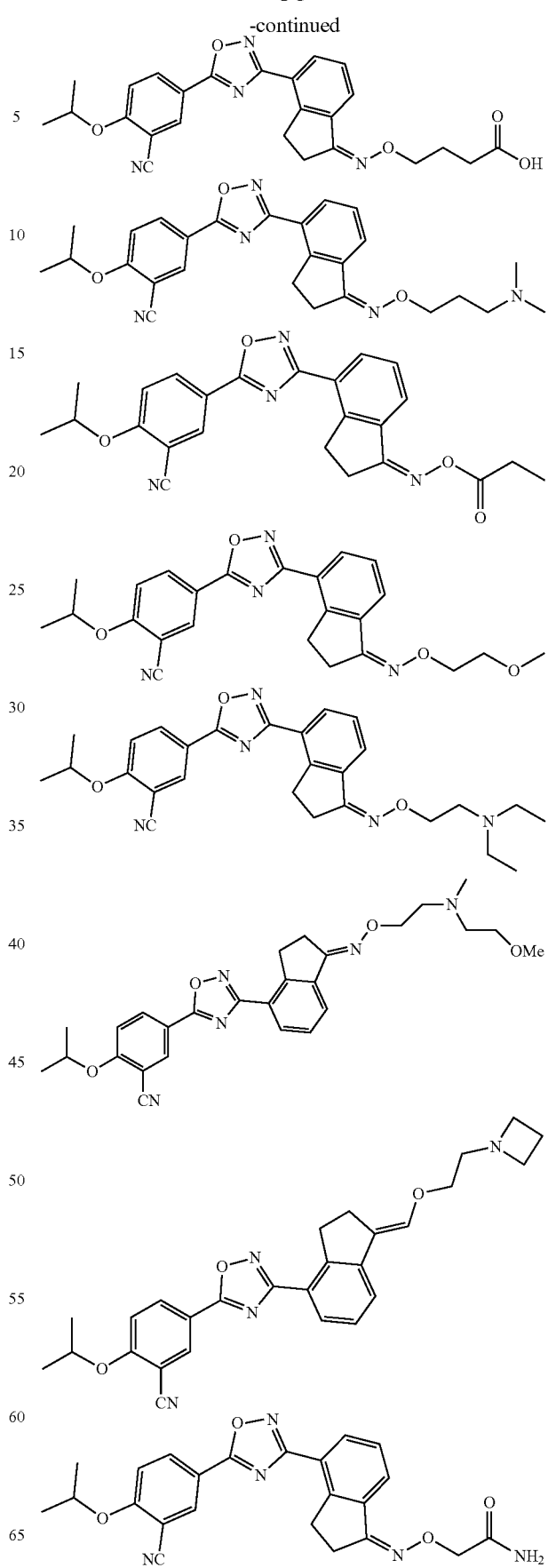

-continued
and
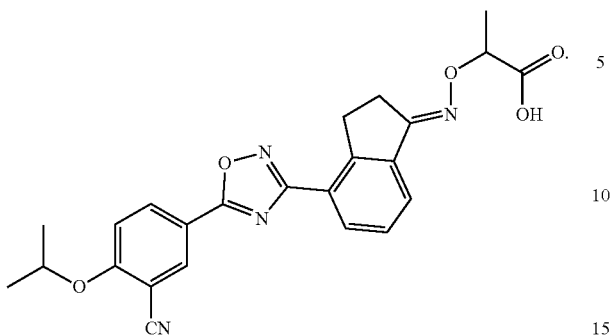

UNITED STATES PATENT AND TRADEMARK OFFICE
CERTIFICATE OF CORRECTION

| | | Page 1 of 2 |
|---|---|---|
| PATENT NO. | : 12,364,686 B2 | |
| APPLICATION NO. | : 17/914707 | |
| DATED | : July 22, 2025 | |
| INVENTOR(S) | : Roger Bakale et al. | |

It is certified that error appears in the above-identified patent and that said Letters Patent is hereby corrected as shown below:

In the Claims

Column 36, Claim 9, Line 63:
"heterocyclealkyl" should read: -- heterocyclylalkyl --.

Column 38, Claim 10, Lines 47-60:

"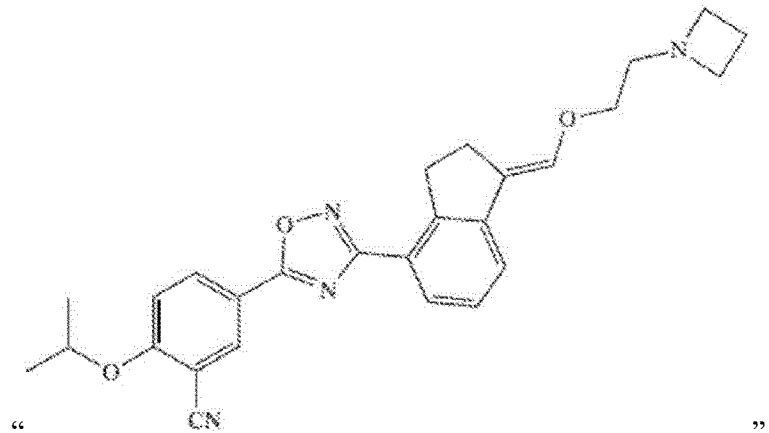"

Should read:

Signed and Sealed this
Fourteenth Day of October, 2025

John A. Squires
*Director of the United States Patent and Trademark Office*

CERTIFICATE OF CORRECTION (continued)

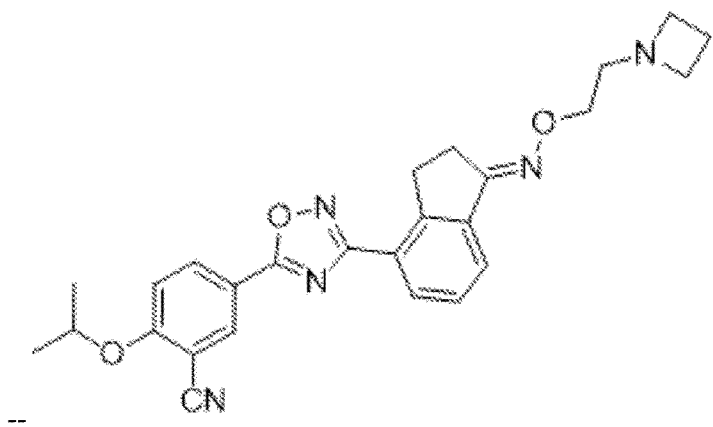

-- --.